United States Patent
Wexler et al.

(10) Patent No.: US 6,259,101 B1
(45) Date of Patent: *Jul. 10, 2001

(54) METHOD AND INSTRUMENTS FOR THE ON-LINE DETECTION, SIZING OR ANALYSIS OF AEROSOL PARTICLES

(75) Inventors: Anthony S. Wexler; Murray V. Johnston, both of Newark, DE (US); Peter Carson, Mays Landing, NJ (US); Ramakrishna Mallina, Newark, DE (US)

(73) Assignee: University of Delaware, Newark, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/935,944

(22) Filed: Sep. 23, 1997

(51) Int. Cl.[7] .............................. H01J 49/00; H01J 49/10
(52) U.S. Cl. .................. 250/423 P; 250/288; 250/287; 250/423 R
(58) Field of Search ................................. 250/287, 288, 250/423 P, 423 R

(56) References Cited

U.S. PATENT DOCUMENTS

| | | | | |
|---|---|---|---|---|
| 4,733,073 | * | 3/1988 | Becker et al. | 250/423 P |
| 4,762,995 | * | 8/1988 | Browner et al. | 250/282 |
| 5,032,722 | * | 7/1991 | Boesl et al. | 250/287 |
| 5,170,053 | * | 12/1992 | Hail et al. | 250/288 |
| 5,382,794 | * | 1/1995 | Downey et al. | 250/288 |
| 5,631,462 | * | 5/1997 | Reemts | 250/287 |
| 5,808,299 | * | 9/1998 | Syage | 250/423 P |

FOREIGN PATENT DOCUMENTS

| | | |
|---|---|---|
| 0 072 375 A1 | 9/1981 | (EP) . |
| 528222 | 10/1940 | (GB) . |
| WO 87/04364 | 7/1987 | (WO) . |

* cited by examiner

Primary Examiner—Jack Berman
Assistant Examiner—Nikita Wells
(74) Attorney, Agent, or Firm—Connolly Bove Lodge and Hutz LLP

(57) ABSTRACT

The present invention is a method for detecting, sizing or otherwise analyzing aerosol particles wherein a beam of radiation (e.g., electromagnetic radiation) interacts with one or more particles in a beam of particles that are traveling in a colinear fashion with the beam of radiation. When the beam of radiation interacts with a particle in the beam of particles, it causes that particle to emit either mass or energy. That mass or energy is then detected by one or more detectors or sensors which provide data that permit the particle to be detected, sized or otherwise analyzed (e.g., the chemical composition of the particle can be determined). The present invention also includes instruments that use the above-described method.

15 Claims, 16 Drawing Sheets

Experimental Apparatus For Aerosol Generation And Size Selection.

Figure 3. Cross-section View of Radial Differential Mobility Analyzer

Resultant Ion Trajectories Of Aerosol Particles Ablated/Ionized At Two Locations Within The Source Region: (a) particle Ablated In The Center Of Source Region (b) particle Ablated 2 cm From Center Of Source Region.

Schematic Diagram Of Mass Spectrometer And Peripheral Data Lines (BS = Variable Dichroic Beam Splitter).

Schematic Diagram Of An Instrument Configured For Simultaneous Measurement Of Positive And Negative Ions.

Resistor Network Used For Floating The Microchannel Plate Detector

Positive Ion Spectra Of 3.5μm, 150nm And 12nm Dia. NaCl Particles Taken At 248nm.

Peak Area Vs. Particle Diameter For The Resultant Ions Na⁺ And K⁺ From NaCl And KCl Particles Respectively. (-X-) Na⁺ Area Count. (-■-) K⁺ Area Count.

Peak Area /Particle Volume Vs Particle Diameter For $Na^+$ (-x-) And $K^+$ (-■-) From NaCl And KCL Particles Repectively.

Averaged positive ion mass spectrum of twenty 150nm dia. NH₄NO₃ particles taken at 248nm Averaged Positive Ion Mass Spectrum Of Twenty 150 nm Dia. Anthracene Particles Taken At 248 nm.

Inlet Transmission Efficiency Vs Particle Diameter

Flow Chart For Data Acquisition Program

METHOD AND INSTRUMENTS FOR THE ON-LINE DETECTION, SIZING OR ANALYSIS OF AEROSOL PARTICLES

The U.S. Government has a paid-up license in this invention and may have the right in limited circumstances to require the patent owner to license others on reasonable terms as provided for by the terms of grant No. ATM-9422993 awarded by the National Science Foundation.

FIELD OF THE INVENTION

The present invention is a method for detecting, sizing or otherwise analyzing aerosol particles wherein a beam of radiation (e.g., electromagnetic radiation) interacts with one or more particles in a beam of particles that are traveling in a colinear fashion with the beam of radiation. When the beam of radiation interacts with a particle in the beam of particles, it causes that particle to emit either mass or energy. That mass or energy is then detected by one or more detectors or sensors which provide data that permit the particle to be detected, sized or otherwise analyzed (e.g., the chemical composition of the particle can be determined). The present invention also includes instruments that use the above-described method.

BACKGROUND OF THE INVENTION

The instruments that are currently available for detecting, sizing or otherwise analyzing aerosol particles with radiation (e.g., electromagnetic radiation) use a design whereby a beam of radiation interacts with particles traveling in a beam of particles so as to cause the particles to emit mass or energy which is then detected and analyzed. The beam of radiation and the beam of particles in these instruments are perpendicular to one another. As discussed hereinafter, this design has disadvantages that are solved by the method of the present invention and the instruments that use that method.

Particles less than 1 $\mu$m in diameter comprise more than 98% of the aerosol population in the atmosphere. Current on-line chemical characterization instruments that use light scattering to detect single particles in-flight are suitable for field studies but cannot detect ultrafine aerosols (i.e., particles with a diameter of less than about 200 nm). An example of this type of instrument is described in U.S. Pat. No. 4,383,171, which issued on May 10, 1983, to Sinha et al.

A solution to this problem was reported by W. D. Reents, Jr., et al. in an article entitled, "Single Particle Characterization by Time-of-Flight Mass Spectrometry", Aerosol Science and Technology 23: 263–270 (1995). The entire disclosure of this article is expressly incorporated herein by reference. In the Reents device, a focused pulsed excimer laser is used to ablate and ionize individual particles without the use of light scattering to sense the presence of a particle, followed by time-of-flight mass spectrometric analysis. By removing the light scattering element of the instrument, Reents was able to detect single particles as small as 0.02 $\mu$m or 20 nm in diameter. However, the fraction of particles that were detected in the particle beam was unsatisfactory.

SUMMARY OF THE INVENTION

The present invention is a method for detecting, sizing or otherwise analyzing aerosol particles wherein a beam of radiation (e.g., electromagnetic radiation) interacts with one or more particles in a beam of particles that are traveling in a colinear fashion with the beam of radiation. When the beam of radiation interacts with a particle in the beam of particles, it causes that particle to emit either mass or energy. That mass or energy is then detected by one or more detectors or sensors which provide data that permit the particle to be detected, sized or otherwise analyzed (e.g., the chemical composition of the particle can be determined). The present invention also includes instruments that use the above-described method. For example, the present invention includes an instrument for the on-line chemical analysis of aerosol particles, especially submicron size aerosol particles. The instrument includes a time-of-flight mass spectrometer wherein an ionization laser beam, which is aligned in a colinear fashion with the beam of particles being analyzed, is free-fired at a high repetition rate to ablate some of the particles and form ions which then travel down a flight tube and contact a detector. The spectra that are produced when ions from the ablated particles contact the detector are recorded and analyzed to determine the identity of the particles that were ablated by the laser.

The instruments of the present invention are designed so that a beam of radiation (e.g., electromagnetic radiation such as a laser beam) interacts with one or more particles in a beam of particles that are traveling in a colinear fashion with the beam of radiation. This design increases the size of the source region, which is the region where the beam of electromagnetic radiation interacts with one or more particles in the beam of particles with sufficient energy to cause the one or more particles to emit mass or energy that can be detected by one or more sensors or detectors. By increasing the size of the source region, the instruments of the present invention are much more likely to have a successful interaction between the beam of radiation and one or more particles (i.e., an interaction that causes the one or more particles to emit mass or energy that can be detected). This in turn means that the instruments of the present invention are much more likely to be able to detect the presence of particles in a sample of gas that contains particles. Further, since the increase in the size of the source region means that the instruments of the present invention will have a greater number of successful interactions between the radiation beam and particles in the particle beam than an equivalent instrument where the radiation beam and particle beam are perpendicular to one another, the instruments of the present invention will obtain more data (i.e., from the detectors or sensors) in a given period of time from a sample of gas containing particles. This results in faster and better detection, sizing or chemical analysis of the particles.

The above-described advantages of using a design where the beam of radiation and the beam of particles are aligned in a colinear fashion is useful in most devices or instruments that use a beam of radiation which interacts with particles in a beam of particles to detect, size or otherwise analyze the particles in the beam. For example, instruments that use atomic emission (e.g., laser induced breakdown spectroscopy), phosphorescence or fluorescence to detect, size or analyze (chemically or otherwise) aerosol particles will be improved by using the method of the present invention wherein the beam of radiation is aligned in a colinear fashion with the beam of particles. In particular, mass spectrometers are improved by using the method of the present invention. In the following paragraphs, a brief summary of the preferred embodiment of the present invention (i.e., a laser mass spectrometer) is provided.

To overcome the limitations of the prior art devices, the time-of-flight mass spectrometer of the present invention was constructed for on-line analysis of aerosols including ultrafine aerosols down to 10 nm and possibly smaller. This instrument, which is field transportable, eliminates the collection and mounting steps normally associated with microprobe analytical methods and is not subject to the particle size limitation inherent with other on-line single particle techniques that use light scattering for particle detection. Instead, the ablation laser is free-fired at a high repetition rate and spectra are saved only when a particle is ablated and ions are formed. The main limitation to free running the laser is a low duty cycle in acquiring spectra. To increase the probability of ablating a particle, the ionization laser beam is aligned colinear with the particle beam giving a much larger ionization region than the currently available instruments which have the ionization laser oriented perpendicular to the particle beam. Modeling of ion trajectories in the mass spectrometer shows that ions produced across the ionization region are efficiently transmitted to a microchannel plate detector.

In the mass spectrometer of the present invention, particles enter the source region of the mass spectrometer through an inlet which confines the particles to a narrow beam. The narrow beam of particles then intersects an excimer laser beam. When a particle is ablated by the laser beam, the ions produced are detected by a detector and mass analyzed. A separate mass spectrum is recorded for each particle and subsequently related to chemical composition. In a preferred embodiment of the present invention, the inlet used is a differentially pumped inlet. In another preferred embodiment of the present invention, the particles are size selected with a differential mobility analyzer (DMA) prior to entering the inlet so that size-dependent changes in the mass spectra can be studied.

DETAILED DESCRIPTION OF THE PREFERRED EMBODIMENT(S)

Figure 1:
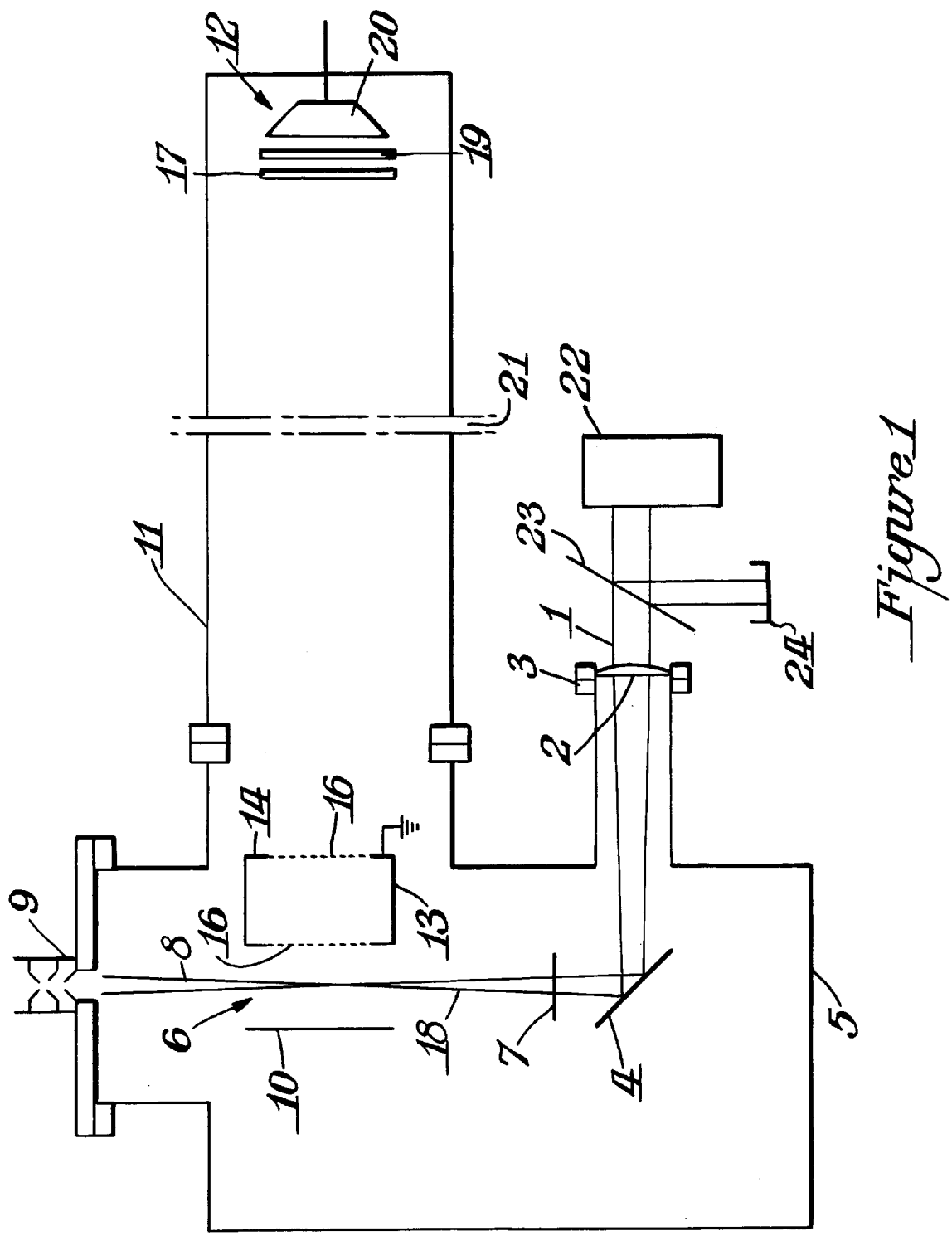
FIG. 1 is a cut-away view of the optical layout of the mass spectrometer used in Example 1.

The preferred embodiment of the present invention is a mass spectrometer which is designed so that a laser beam, which interacts with particles in a particle beam, is aligned in a colinear fashion with the beam of particles.

The time-of-flight mass spectrometer of the present invention was constructed for on-line analysis of aerosols including ultrafine aerosols down to 10 nm and possibly smaller. This instrument, which is field transportable, eliminates the collection and mounting steps normally associated with microprobe analytical methods and is not subject to the particle size limitation inherent with other on-line single particle techniques that use light scattering for particle detection. Instead, the ablation laser is free-fired at a high repetition rate and spectra are saved only when a particle is ablated and ions are formed. The main limitation to free running the laser is a low duty cycle in acquiring spectra. To increase the probability of ablating a particle, the ionization laser beam is aligned colinear with the particle beam giving a much larger ionization region than the currently available instruments which have the ionization laser oriented perpendicular to the particle beam. Modeling of ion trajectories in the mass spectrometer shows that ions produced across the ionization region are efficiently transmitted to a microchannel plate detector.

In the mass spectrometer of the present invention, particles enter the source region of the mass spectrometer through an inlet which confines the particles to a narrow beam. The narrow beam of particles then intersects an excimer laser beam. When a particle is ablated by the laser beam, the ions produced are detected by a detector and mass analyzed. A separate mass spectrum is recorded for each particle and subsequently related to chemical composition. In a preferred embodiment of the present invention, the inlet used is a differentially pumped inlet. In another preferred embodiment of the present invention, the particles are size selected with a differential mobility analyzer (DMA) prior to entering the inlet so that size-dependent changes in the mass spectra can be studied.

The instrument of the present invention can be used for the on-line analysis of aerosols containing particles ranging in size from about 10 $\mu$m to 10 nm. In a preferred embodiment of the present invention, the instrument is used to analyze submicron size particles, especially ultrafine particles (i.e., particles with a diameter of less than about 200 nm).

To analyze these ultrafine particles, the particle detection laser that is normally used in the prior art devices was eliminated in the design of the instrument of the present invention and the excimer laser is free fired. By eliminating the particle detection laser, the analysis is no longer limited to the 0.2 $\mu$m particle diameter detection limit of the light scattering instrumentation. Free running the ablation laser results in a low duty cycle for acquiring spectra, since only a small fraction of the laser shots actually ablate a particle. To reduce the number of laser shots between acquiring spectra, the effective ionization region is maximized by aligning the laser beam and particle beam to be colinear. For convenience of design, the laser beam and particle beam are preferably oriented so that they are colinear but traveling in opposite directions (i.e., the laser beam and particle beam are oriented so as to cause a head-on collision of the particles with the laser beam).

The optical alignment is shown in FIG. 1, which shows the system that was used in Example 1. The laser enters the vacuum chamber through a focusing lens mounted in a conflat port. A mirror is positioned inside the vacuum chamber and is aligned at a 45° angle to reflect the incoming laser beam vertically through the source region. A quartz slide positioned above the mirror is used to prevent particles from depositing on the mirror surface. Cleaning the quartz slide is rarely necessary because the laser tends to vaporize particles deposited on the slide without leaving a residue. The laser pulse energy in the source region was found to degrade less than 10% after 100 hours of operation. The laser beam is imaged to a small spot (e.g., about 600 $\mu$m in diameter in the device shown in FIG. 1) in the center of the source region but expands to a much larger spot (e.g., about 2 mm in diameter) at the edges of the source region.

With the optical setup shown in FIG. 1, and a median particle beam diameter of, for example, 0.5 mm throughout the source region, the limiting factor for acquiring spectra is the maximum length of the source region, the region over which laser produced ions can be efficiently transmitted to the microchannel plate detector. By positioning the laser beam along a vertical path (i.e., a path that is colinear with the particle beam), the interaction region between the laser and particle beams is much larger than that which would be obtained with a horizontal laser beam path (i.e., a laser beam path that is perpendicular to the particle beam). For example, in the device shown in FIG. 1 and described in Example 1, the median particle beam diameter was 0.5 mm and the source region (i.e., the region over which laser produced ions can be efficiently transmitted to the detector) was 4.0 cm, which is an eighty fold increase of the interaction volume over that which would be obtained with a horizontal laser beam path (i.e., where the laser beam path is perpendicular to the particle beam path).

The particle ablation efficiency ($E_a$) is defined as the number of particles ablated and analyzed divided by the number of particles entering the source region:

$$E_a = (Lf/100v) \cdot (Q_{laser}/Q_{part})$$

where $v$ is the particle velocity, $f$ is the frequency of data collection, L is the length of the source region, and $Q_{part}$ and $Q_{laser}$ are the volume of the particle beam and laser beam, respectively, in the source region. This equation assumes that the particle beam is larger than the laser beam. If the particle beam is contained within the laser beam, then the $Q_{laser}/Q_{part}$ term is replaced by 1. For the instrument described in Example 1, $Q_{laser}/Q_{part}$ is 0.0007. The velocity of the particles through the inlet is estimated as the speed of sound (500 m/s) since a critical orifice is used in the inlet. The length of the source region, L, is 4 cm as discussed in Example 1. The frequency of data collection, $f$ is given by the maximum rate for the data acquisition system, 30 Hz for the system described in Example 1. Thus, the particle ablation efficiency for the source region configuration used in Example 1 is estimated to be $1.7 \times 10^{-8}$.

A differential mobility analyzer (DMA) separates particles by their electric mobility (see Knutson, E. O. and Whitby, K. T., J. Aerosol Sci., 6, pages 443 and 453 (1975)). The electric mobility is related to the particle mass to charge ratio (i.e., m/z ratio). If the average charge on the particles is constant (typically 1 when Boltzmann charging is used), then the electric mobility is directly proportional to particle mass and therefore is related to particle size.

In a preferred embodiment of the present invention, a DMA is inserted before the aerosol inlet to select a narrow size distribution for analysis. This enables the user to correlate the particle size with the mass spectra. There are two basic DMA designs used currently, the concentric cylindrical configuration and the radial flow configuration (see Fission, H.; Hummes, D.; Stratmann, F.; Buscher, P and Neumann, S.; Aerosol Sci. Technol. 1996,1,1). The concentric cylindrical design introduces the aerosol and sheath air from one end of a cylinder and the aerosol passes an electrode on the way to two exit ports. The excess exit port flow rate equals the sheath flow rate and this is where the large particles exit the DMA. A narrow band of particles with the correct mobility remain with the aerosol flow and pass through the monodisperse exit port. Smaller particles collect on the electrode and are not transmitted through either exit port. In the radial flow configuration, the aerosol flow and sheath flow enter through the outer edges of two parallel plates. Large particles are carried out the excess flow port, while the particles with the correct mobility migrate across the sheath flow and are transmitted through the monodisperse exit port. Smaller particles collect on the electrode and are not transmitted through either port. The radial differential nobility analyzer was selected for this work because of its ease of fabrication.

Figure 2:
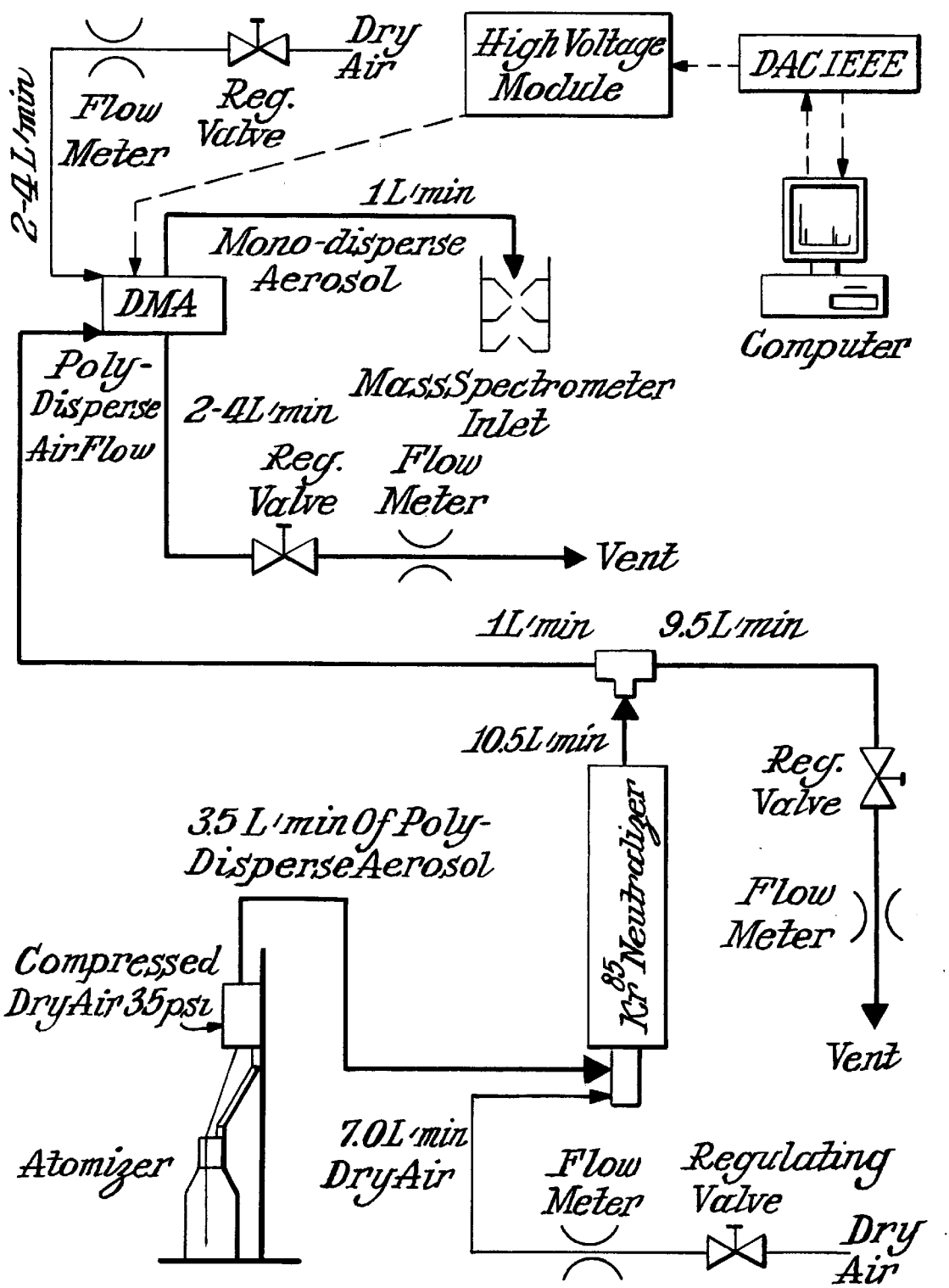
FIG. 2 is a schematic of a preferred DMA system for use with the mass spectrometer of the present invention.

FIG. 2 shows a preferred DMA system for use with the mass spectrometer of the present invention. As shown in FIG. 2, particles are produced with an atomizer and then passed through a $^{85}$Kr neutralizer before entering the DMA. An additional 7.0 L/min of dry air is added to the aerosol flow before the $^{85}$Kr neutralizer to dry the primary droplets produced from the atomizer. The neutralizer works by producing both positive and negative ions in air that are attracted to oppositely charged aerosol particles. The final charge distribution on the particles is characterized by the Boltzmann equilibrium shown in Table 1 (obtained from TSI Model 3054 Aerosol Neutralizer Manual, 1990, 3).

TABLE 1

| | | | Distribution of Percent of Particles Carrying $n_p$ Elementary Charge Units | | | | | | |
|---|---|---|---|---|---|---|---|---|---|
| Dp($\mu$m) | $n_p = -4$ | $-3$ | $-2$ | $-1$ | 0 | 1 | 2 | 3 | 4 |
| 0.01 | | | | 0.34 | 99.32 | 0.34 | | | |
| 0.02 | | | | 5.23 | 89.53 | 5.23 | | | |
| 0.04 | | | 0.23 | 16.22 | 67.11 | 16.22 | 0.23 | | |
| 0.06 | | 0.01 | 1.25 | 21.31 | 54.88 | 21.31 | 1.25 | 0.01 | |
| 0.08 | 0.08 | 2.78 | 23.37 | 47.53 | 23.37 | 2.78 | 0.08 | | |
| 0.1 | 0.26 | 4.39 | 24.09 | 42.52 | 24.09 | 4.39 | 0.26 | | |

TABLE 1-continued

Distribution of Percent of Particles Carrying $n_p$ Elementary Charge Units

| Dp($\mu$m) | $n_p$ = -4 | -3 | -2 | -1 | 0 | 1 | 2 | 3 | 4 |
|---|---|---|---|---|---|---|---|---|---|
| 0.2 | 0.32 | 2.33 | 9.66 | 22.63 | 30.06 | 22.63 | 9.66 | 2.33 | 0.32 |
| 0.6 | 3.82 | 7.41 | 11.89 | 15.79 | 17.36 | 15.79 | 11.89 | 7.41 | 3.87 |
| 1 | 5.42 | 8.06 | 10.71 | 12.71 | 13.45 | 12.71 | 10.71 | 8.06 | 5.42 |

From Table 1, it can be seen that Boltzmann charging is most efficient for aerosol particles within the size range of 40 nm to 200 nm. For larger particles, the high proportion of multiply charged particles becomes significant causing the simple correlation between electric mobility and particle diameter break down. Aerosol particles smaller than 40 nm have a low probability of charging and as a result, very few are transmitted through the DMA.

Figure 3:
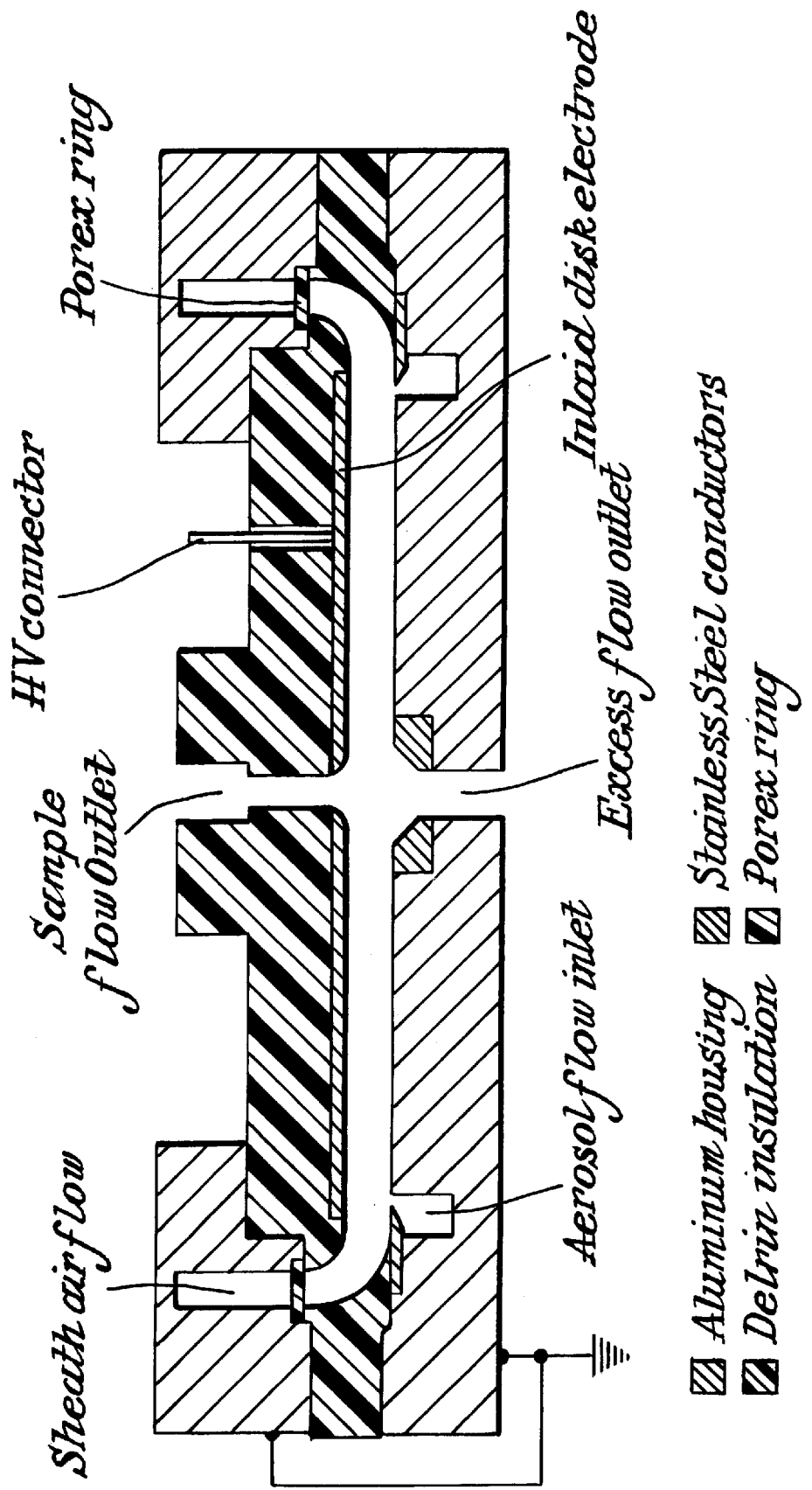
FIG. 3 is a cross-sectional view of the radial differential mobility analyzer used in Example 1.

FIG. 3 is a cross-sectional view of the radial differential mobility analyzer used in Example 1. Sheath air at 2–4 L/min enters tangentially into a circular channel and passes through a porex ring that restricts the air flow and produces a uniform flow field. A flow of particles suspended in an airflow of 1 L/min enters tangentially through a second circular channel and passes through a 1.2 mm gap that provides a turbulence free combination of the sheath and aerosol air flows. The particles then pass by the electrode toward the outlets. The electrode is made of stainless steel and the rounded housing plate opposite of the electrode is made of aluminum. Typical voltages applied to this electrode at atmospheric pressure vary from 50 volts to 8600 volts to transmit particles between 12 nm and 250 nm, respectively, when the sheath air flow is 2 L/min and the particle air flow is 1 L/min. The electric field generated by the electrode causes negatively charged aerosol particles to migrate across the sheath air flow toward the electrode. Particles having the selected mobility and hence the correct mass-to-charge ratio exit through the sample output (i.e., the sample flow outlet) at an air flow rate of 1 L/min. Particles with a high mass-to-charge ratio exit through the excess flow outlet at the same flow rate as the incoming sheath air while particles with a low mass-to-charge ratio collect on the electrode.

The DMA used in Example 1 was calibrated with a NaCl aerosol. A 3.5 L/min air and aerosol mixture was produced by nebulizing a 0.02 M solution of NaCl with an atomizer (TSI, model 3075). The aerosol was then dried with a diffusion drier and passed through a $^{85}$Kr neutralizer to produce a bipolar charge distribution of the particles. A regulated flow of 1 L/min (total flow of 3.5 L/min) of the dried aerosol entered the DMA after passing through the $^{85}$Kr neutralizer. The flow was regulated by maintaining a flow rate of 2.5 L/min to a vent. Sheath air flows of 2 L/min and 4 L/min were used for calibration and were controlled with a regulating flow meter. The excess flow from the DMA was directly vented to a fume hood. A monodisperse aerosol flow from the DMA entered directly into a commercial DMA (Model 307104, TSI, St. Paul, Minn.) which had the input flow set at 1 L/min. All other air flows in the commercial DMA were internally controlled and the monodisperse aerosol flow was directly connected to the input of a condensation nucleus counter (Model 3025, TSI, St. Paul, Minn.). The voltages applied to the radial DMA were produced by a high voltage module that had an output range of 0 to 8600 volts. An IBM compatible computer ran the TSI scanning Mobility Particle Sizer version 2.0 (SMPS) software that automatically controlled the voltage scan of the commercial DMA and collected the particle counts from the condensation nucleus counter (CNC). After running a scan, the SMPS software saved the particle count as a function of particle size to a file on the computer hard disk. The radial DMA was calibrated by stepping the electrode voltage from 200 to 8600 volts. For each voltage setting, the commercial DMA was scanned to monitor the particles transmitted through the radial DMA.

The calibration results for the radial DMA with sheath air flows of 2 and 4 L/min showed that the 4 L/min sheath air flow transmits a 50% narrower size range through the DMA than does the 2 L/min sheath air flow.

As can be seen from the discussion above, and the Examples provided later in this patent application, a variety of inlet designs can be used in the instrument of the present invention. The preferred inlet design will depend on the effect that the user wishes to obtain. For example, if the user simply wants to limit the spread of the particles and obtain a focused particle beam, a number of different inlet designs could be used, such as the inlet designs shown in the Reents, Jr. et al. article (cited earlier); U.S. Pat. No. 4,383,171, which issued on May 10, 1983 to Sinha et al.; U.S. Pat. No. 5,270,542, which issued on Dec. 14, 1993 to McMurry et al.; and U.S. Pat. No. 5,565,677, which issued on Oct. 15, 1996, to Wexler et al. The entire disclosures of all of these patents are hereby expressly incorporated by reference into the present application. As discussed above, if the user wanted to select a narrow size distribution of particles for analysis, a DMA can be inserted before the inlet. An artisan of ordinary skill would understand that additional modifications can be made to the inlet design to obtain different effects that are known in the art.

One of the primary concerns with the laser optical layout is the ability to collect ions produced anywhere in the source region and transmit them to the detector. The mass spectrometer was designed using the programs SIMTOF and SIMION 6.0 to model and optimize the ion flight times and trajectories. SIMTOF was used to optimize the source region configuration and voltages for maximum mass resolution. Simulations with SIMTOF determined that a one meter flight tube was necessary to achieve a resolution of 250.

SIMION models the ion trajectories through the mass spectrometer. In using SIMION the following assumptions were made: the flight tube was one meter and ions produced by laser ablation had an initial 1 eV kinetic energy with equal probability in all directions. All ions were accelerated with the additional 4300 eV kinetic energy in the direction toward the detector to simulate the electric field effects from the source region.

Figure 4:
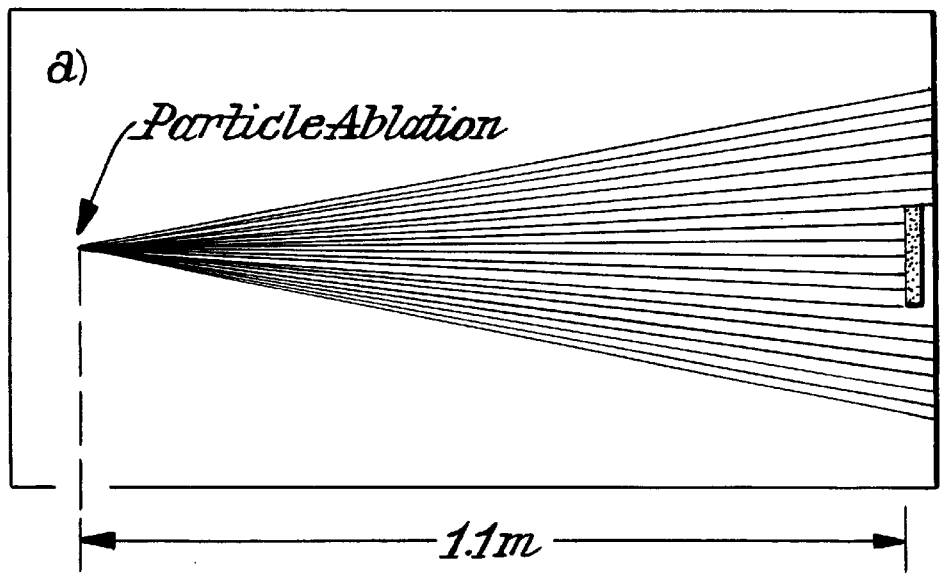
FIG. 4 shows the SIMION ion trajectory for ions originating in the center of the ion optics.
Figure 5:
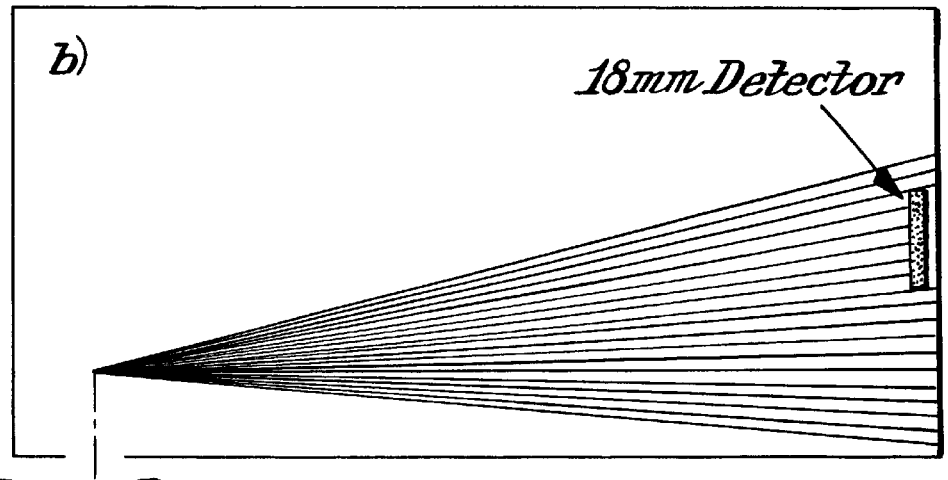
FIG. 5 shows the SIMION ion trajectory for ions originating at 2 cm from the center of the ion optics.

SIMION modeling showed that the ion plume will expand to 5 cm diameter by the time it reaches the detector. Since the microchannel plate diameter used in Example 1 was only 18 mm, particles ablated up to 2 cm in either direction from the center of the source region produced a constant number of ions that reached the detector. FIGS. 4 and 5 show the SIMION (SIMION 30 version 6.0, Idaho National Engineering laboratory, Idaho Falls, Id.) ion trajectories for ions originating in the center (FIG. 4) and at 2 cm from the center of the ion optics (FIG. 5). Most of the ions outside of this 4 cm source region do not strike the microchannel plate detector. Within the 4 cm region, 15% of the ions produced in the source region were found to strike the detector independent of particle location within the source region.

The modeling led to the conclusion that a source assembly consisting of three plates representing the repeller, acceleration and grounding plates was the simplest and the best design. The actual source assembly was built with 4.4 cm×7.5 cm electrode plates (e.g., stainless steel plates). Within these plates are ½ cm×5 cm centered rectangular (cut-out) holes that have a 90% transmittance wire mesh spot welded over the plate surface to reduce the electric field distortions.

Ion focusing and resolution enhancement designs typically used in other applications, such as the einzel lens and angular reflectron, seemed to work only when the ion-plume originated near the center of the source region. With these focusing techniques, ion transmission to the detector degraded quickly when the ions were produced more than 0.5 cm from the center of the source region.

FIG. 1 shows the mass spectrometer used in Example 1. The linear mass analyzer consists of a 1.1 m flight tube 11 and a dual microchannel plate detector 12. The source region consists of repeller plate 10, acceleration plate 13 and a grounding plate 14 with a ½" spacing between the plates. The potentials across the plates are given in table 2 for both positive and negative ion modes.

TABLE 2

Voltages for Mass Spectrometer Operation

| Electrode | Voltages in positive ion mode | Voltages in negative ion mode |
|---|---|---|
| Repeller plate | +5000V | −5000V |
| Acceleration plate | +2700V | −2700V |
| Drift tube | 0V | 0V |
| Microchannel plate detector | −2200V | −2200V |

An effective laser and ion optic configuration, a narrow particle beam within the source region and a fast data system are essential for optimizing the mass spectrometer to work efficiently with little time delay between acquiring spectra. The first requirement, an effective laser and ion optical setup, has already been discussed. The second requirement, a narrow particle beam is obtained by using an inlet design that meets the particular needs of the user, as discussed earlier. The third requirement, a fast data system, is discussed here. The fastest data system that could be purchased off-the-shelf is a Tektronix 520A oscilloscope. This oscilloscope samples 5 Kb record lengths at 70 Hz or 15 Kb record lengths at 30 Hz. The 5 Kb record length at 500 Ms/s only allows ions up to m/z 50 (i.e., mass/charge ratio of 50) to be detected and cannot be used for most applications. In contrast, the 15 Kb record length corresponds to a mass range of 0–250 daltons. Spectra are digitized by the oscilloscope and checked to see if any peak registered above a minimum threshold. When this occurs, the oscilloscope transfers the spectrum to a computer for storage. This scheme works fine for the particle density produced by the atomizer used in Example 1 ($10^5$ particles/$cm^3$), but is not practical for the particle density produced by the vibrating orifice aerosol generator (VOG Model No. 3450, manufactured by TSI, Minneapolis, Minn.—100 particles/$cm^3$). Hit rates achieved when using the atomizer for particle generation are 3 particles per minute, whereas hit rates of 3 particles per hour are common for the vibrating orifice aerosol generator.

To solve this problem, an A/D (analog to digital) conversion board was developed with Precision Instruments of Knoxville, Tenn. This board (9847-500 with the "data available option") will replace the oscilloscope and will allow a sampling rate of 100 Hz with 16 Kb record lengths. When this board is used, the excimer laser can be fired at 100 Hz.

The analysis of both the positive and negative ions from the same particle is useful in analyzing unknown aerosols. Having only positive or negative spectrum of a particle does not permit complete classification. For example, compounds such as $NH_4NO_3$ and $NaNO_3$ have very similar negative ion mass spectra whereas positive ion mass spectra have unique peaks ($Na^+$ vs. $NH_4^+$). However, for some purposes, it is satisfactory to only analyze the positive ion mass spectra.

An instrument capable of simultaneously measuring the positive and negative mass spectra for a single micron size particle has been reported (see Hinz, K.; Kaufman, R.; Spengler, B.; Aerosol Sci. Technol., 1996, 4, 233). The combination of positive and negative mass spectra aids pattern recognition techniques such as principal component analysis (PCA) for the analysis of mass spectra. However, negative mass spectra are typically harder to acquire than their positive counterparts and require a higher ablation laser pulse energy and a higher gain on the detector. Negatively charged molecular ions in laser ablation mass spectra are thought to be produced by electron capture. In the negative mass spectra, electrons are observed indicating that many electrons produced by the ablation process are not captured. When submicron sized aerosols are analyzed, the resultant ion plume becomes less dense and the electron capture probability is reduced. For particles composed of KCl, NaCl, $NH_4NO_3$ and anithracene and ranging in size from 12 nm to 150 nm, only KCl consistently gave negative ion mass spectra. In contrast NaCl and $NH_4NO_3$ produced detectable negative ion mass spectra at only 5% of the rate for the corresponding positive ions. Increasing the laser irradiance may increase the electron capture probability and therefore the negative ion yield by producing a more dense plume.

Figure 6:
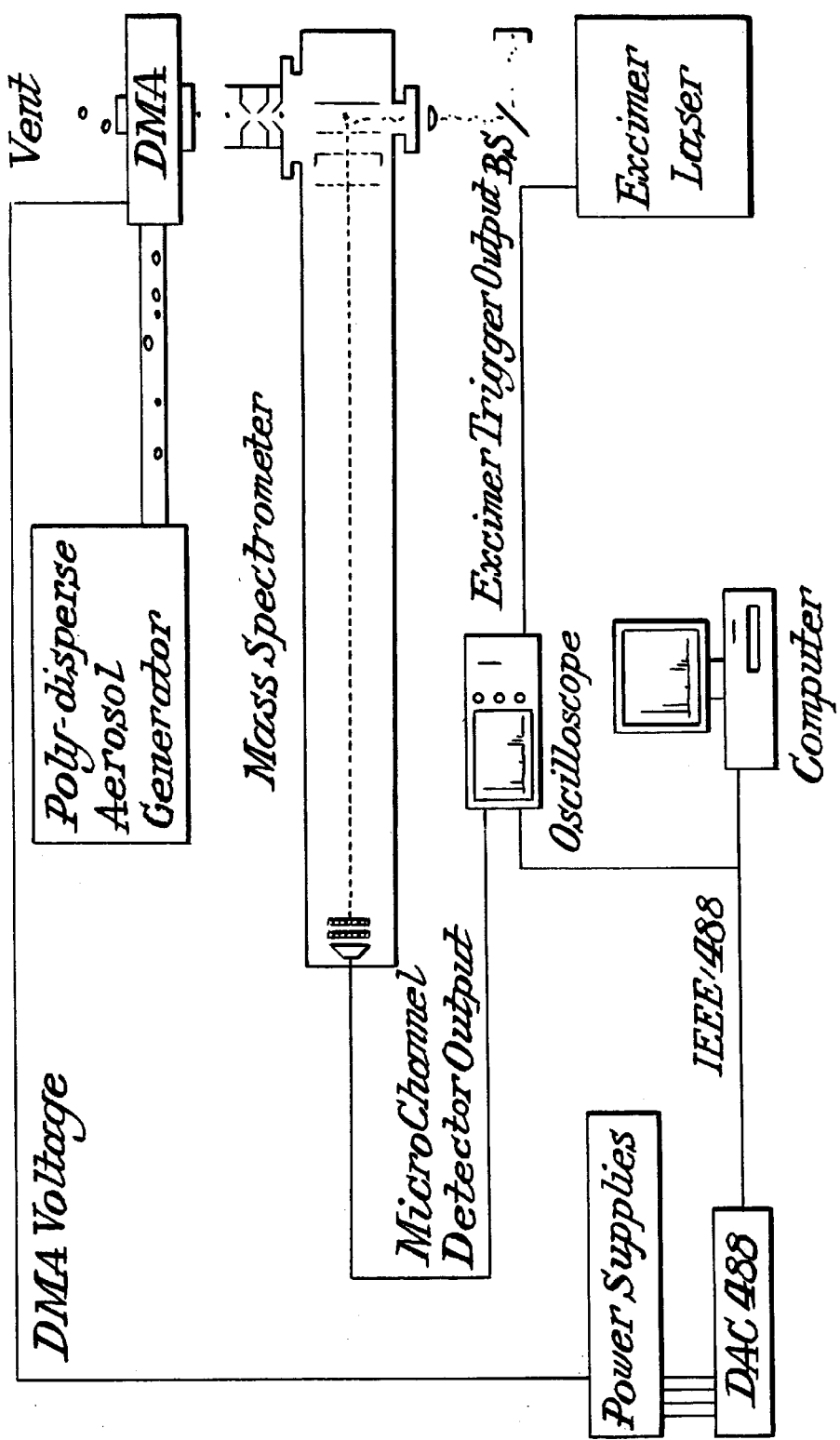
FIG. 6 is a schematic diagram of a mass spectrometer of the present invention and its peripheral data lines.
Figure 7:
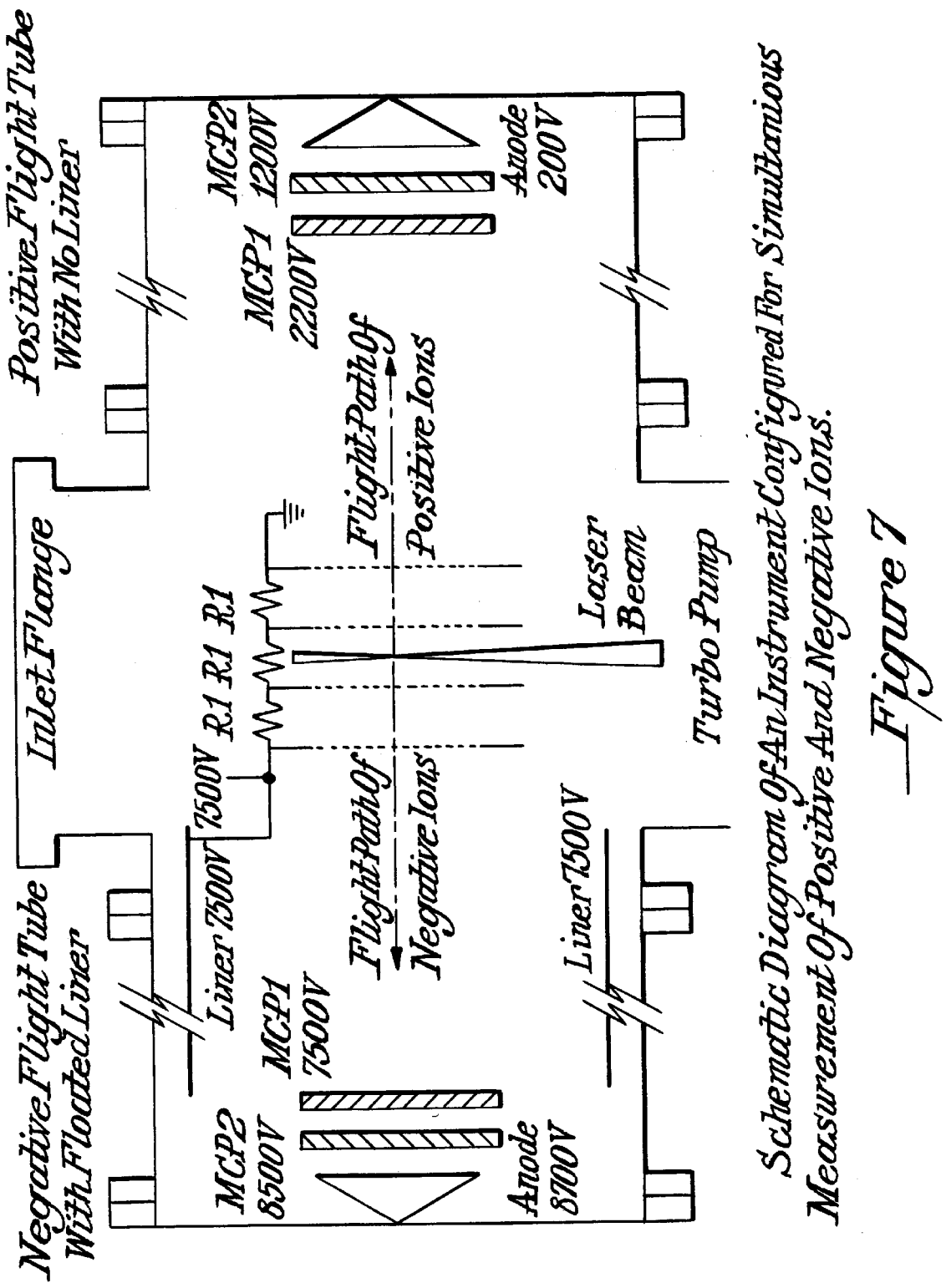
FIG. 7 is a schematic diagram of a modified version of the instrument that is configured for the simultaneous measurement of positive and negative ions.
Figure 8:
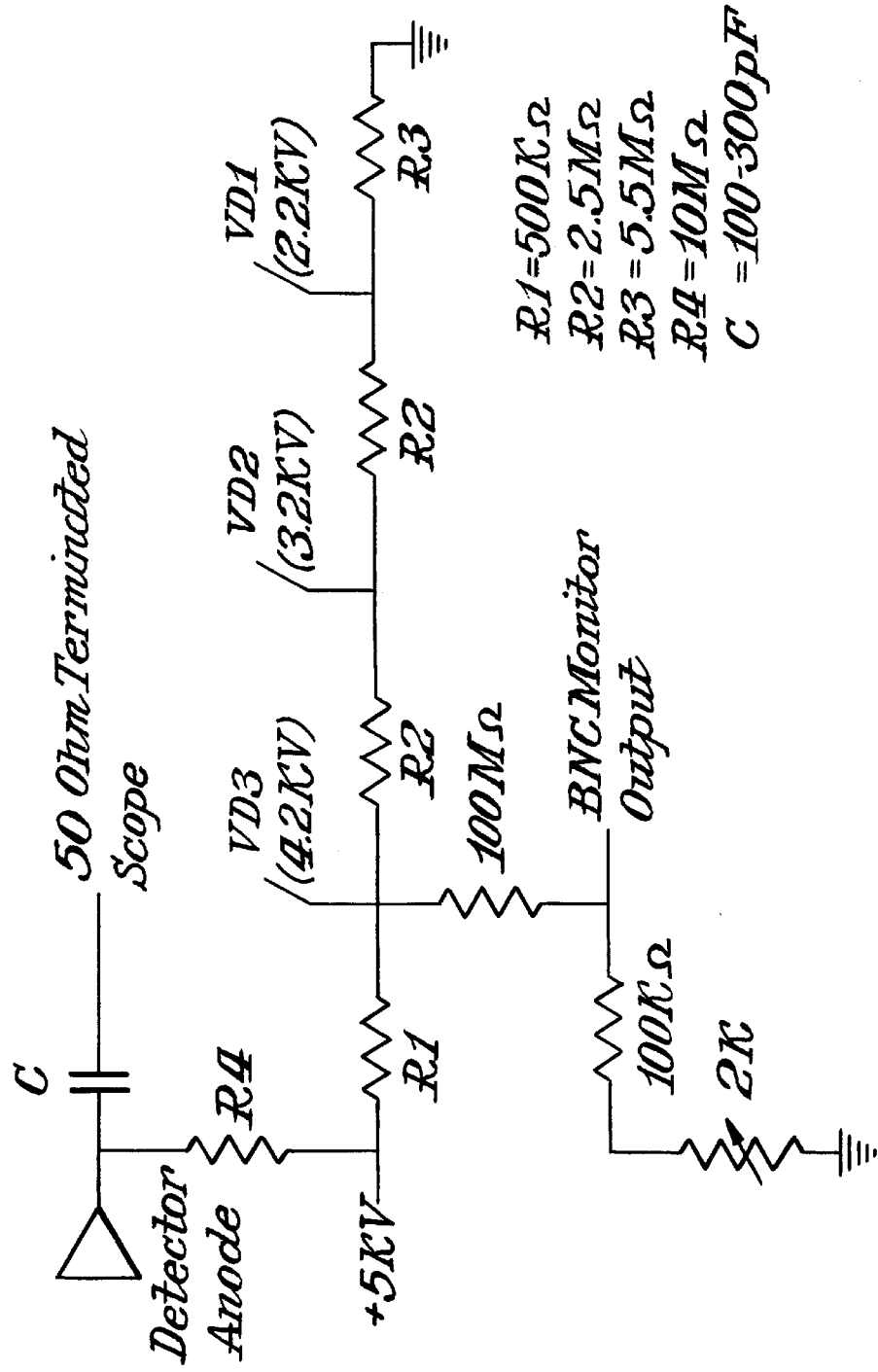
FIG. 8 is a schematic of the resistor network used for floating the microchannel plate detector.

The ability to analyze both positive and negative ions separately has been incorporated into the design of the instrument in FIG. 6. That is, although the instrument is normally configured to analyze positive ions, it can be quickly reconfigured to test for negative ions. FIG. 7 is a schematic of a modified version of the instrument for simultaneously analyzing both positive and negative ions. Relative to the instrument shown in FIG. 6, three changes have been made. First, a fourth source region plate was added to the mass spectrometer. This plate aids in the extraction of the negative ions. Second, a second flight tube (negative flight tube) with a floated liner and detector system was added, the liner was held at the same potential as the fourth plate (negative acceleration plate 2) to prevent the ions from straying away from their original flight path to the detector. Third, the detector has to be floated with the anode AC coupled to the oscilloscope. A schematic of the voltage divider used for floating the detector is shown in FIG. 8. The purpose of the capacitor is to allow only the AC components of the signal to reach the oscilloscope while preventing the DC high voltage from reaching the oscilloscope. Table 3 lists the plate and detector voltages for the positive and negative drift tubes, source region and the detectors.

TABLE 3

Voltages Applied to the Ion Optics and Microchannel Plate Detectors

| Electrode | Voltages |
|---|---|
| Positive acceleration plate 1 | +2500V |
| Positive acceleration plate 2 | 0V |
| Positive ion drift tube | 0V |
| Positive detector MCP 1 | −2200V |
| Positive detector MCP 2 | −1200V |
| Positive detector anode | 0V |
| Negative acceleration plate 1 | +5000V |
| Negative acceleration plate 2 | +7500V |
| Negative ion drift tube | +7500V |
| Negative detector MCP 1 | +7500V |
| Negative detector MCP 2 | +8500V |
| Negative detector anode | +8700V |

Floating the detector at a high voltage also has some disadvantages and that is why all previous negative ion mass spectra were taken with a detector not floated. With the double flight tube assembly, floating the detector is necessary. The effect of floating the detector on the mass spectra is discussed below. As stated previously, most time-of-flight detectors have negative voltages applied across the microchannel plates with the first plate having the highest voltage and the anode having the lowest voltage. When the detector is floated, not only is the polarity of the potential switched from negative to positive, but now the anode has the highest voltage and the first microchannel plate is grounded. The main undesirable effect arises from the high pass filter produced from the coupling of the capacitor with the terminating resistor shown in FIG. 8. The response of the high pass filter is characterized by the following equation:

$$1/t = RC$$

The ringing of the floated detector becomes apparent when compared to the normal detector configuration response. The ringing originates from the discrepancy between the high pass filter's resistance and the oscilloscope's terminating resistance. The capacitor on the detector side cannot be coupled to a 50 Ω resistor because of the low output current of the power supply. The oscilloscope was switched to a 1 MΩ internal terminated resistance to match the resistance of the detector resistance but the response of the oscilloscope acted as an integrator and summed all input voltages and produced worthless spectra. Also, when the detector is floated, the spectra are artificially narrowed. This occurs because the high pass filter passes high frequency components of the signal while preventing the low frequency or DC components from reaching the detector. This results in some loss of low frequency components associated with the peak. The value of 100 µF is chosen for the capacitor for quick response and its high pass of DC voltage.

In the instrument of the present invention, the particles to be analyzed are separated from the surrounding gas before they enter the mass spectrometer as a particle beam. Inside the mass spectrometer, the particles are individually analyzed. The number of particles analyzed by the instrument per second depends on their ambient concentration and size distribution, but as described in more detail below, under typical urban conditions particles will be analyzed at a rate of roughly one per second. One operating protocol would be to sample 100 particles at each of 10 sizes over the 10 nm to 2 micron range, then cycle through again. If we average one particle per second, each cycle would take 1000 seconds or about 15 minutes. So temporal resolution is about one second, but a statistically significant size distribution would take about 10 to 20 minutes to obtain.

In a preferred embodiment of the present invention, as discussed above, the particles entering the mass spectrometer are sized by using a neutralizer-DMA combination to select particles by mobility. In a highly preferred embodiment of the present invention, the particles entering the mass spectrometer are sized by using a size-selective nozzle.

There is a growing body of work on focusing aerosol particles by passing them through an orifice (e.g., Fernandez de la Mora and Riesco-Chueca, 1988; Liu et al., 1995 a, b: Gomez-Moreno and Fernandez de la Mora, 1996). In general terms, particles are focused if their Stokes number is approximately one, where the Stokes number is defined by $$Stk = U\tau/D$$

and where U is the characteristic radial velocity at the orifice and in this work is near sonic, D is the orifice diameter, and $\tau$ is the particle relaxation time. Particles with much larger Stokes number cross the centerline before the focal point and over a wide range of spatial locations. Particles with Stokes number much smaller than one are not effectively brought to the centerline. Since only a narrow range of particle Stokes numbers are focussed, this feature can be used to select an aerodynamic particle size.

The design of size-selective nozzles is based on the observation that the largest velocities and smallest orifice diameters will focus particles with the shortest relaxation times—that is, large velocities and small orifice diameters are required to focus small particles, analogous to the design of impactor systems. The largest velocities will correspond to a choked flow wherein the velocities are sonic. Thus the aerosol must pass through a choked orifice before the particles enter the source region and this orifice will focus the smallest possible particle sizes.

The ideal nozzle will transmit the largest possible volume flow rate so that particles are sampled as frequently as possible. Thus the orifice diameter is fixed at the largest size that can focus particles into the excimer laser beam. In the instrument of the present invention, the laser beam propagates up from the bottom of the source region, while the particle beam propagates down from the top. The laser beam is focused to a 600 micron diameter spot in the middle of the 4 cm source region, and it widens to a 2 mm diameter at the top and bottom boundaries of the source region. The poor beam quality from the excimer laser does not permit a more focussed beam and since we want to have the maximum power density in the source region, we do not want to make the beam wider.

Numerous fluid flow calculations have been performed using NPARC 2.2B (NPARC, 1995), a code developed and used by NASA to simulate compressible fluid flows, to show that a 3 mm orifice is near optimum. Simulations with this code also illustrated how the radial velocity, U, varies with pressure upstream of the orifice. The velocity is basically independent of pressure down to about 50 torr after which it drops off.

Fernandez de la Mora and coworkers (1996) have shown that varying the orifice diameter in an impactor changes the Cutpoinit location due to the shift in Stokes number. But they found that only modest changes in orifice size were possible while maintaining a well sealed system. This led to only a modest change in the cutpoint diameter, less than a factor of two in diameter. Thus, we can select particle size by changing the orifice diameter, but the diameter range accessible this way is modest.

So far we have determined that the orifice diameter is essentially fixed at its largest value that can be focussed into the laser beam, and the fluid velocity is dependent on pressure, but relatively constant over a wide range of upstream pressures. Then the only remaining Stokes number parameter than can be varied to select particle size is the relaxation time, and pressure upstream of the orifice is the only parameter that is directly controllable over a wide dynamic range. The relaxation time can be written as $$\tau = \rho_p d^2 C_C / 8\mu$$

assuming that the particle is spherical, where $\tau_p$ is the particle density, d is the particle diameter, $C_C$ is the Cunningham correction factor, and $\mu$ is the viscosity of air. The particle density and diameter are not under our control and James Clerk Maxwell proved that the viscosity of an ideal gas is independent of pressure (Moore, 1972) so the Cunningham correction factor is the only parameter that can be varied. The slip correction factor can be written as $$C_C = 1 + 2/(Pd)[6.32 + 2.01 \exp(-0.1095 \, Pd)]$$

where P is the pressure upstream of the orifice in torr (Sioutas et al., 1994). Over a reasonable range of pressures, the critical orifice can focus a wide range of particle sizes.

Figure 9:
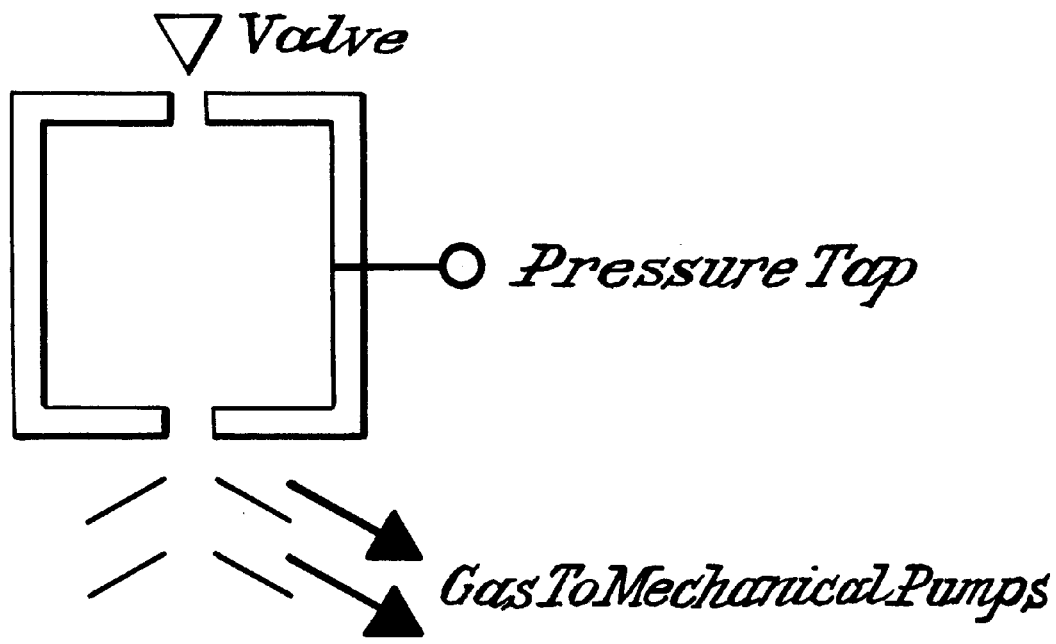
FIG. 9 is a schematic of a preferred nozzle for the mass spectrometer.

A schematic of a preferred nozzle design is shown in FIG. 9. There is a constricting valve that controls the air flow into a low-pressure region. The flow will be choked and sonic at the constriction, but the large ambient pressure and careful aerodynamic design should minimize particle deposition there. The valve will be computer controlled to alter the flow rate, and therefore the pressure, in the nozzle body. A pressure sensor, monitored by computer, will indicate the pressure in the low-pressure region and will indicate which particle size range is focussed. Skimmers after the critical orifice will remove most of the gas so that the turbo pumps can maintain the desired sub-microtorr pressure in the source region.

The key characteristics of the nozzle will be its size selectivity and the volume of gas that is processed. Greater volumes of gas will result in more frequent particle hits. Wider size selectivity will focus more particles but result in less precision on particle diameter sampled. When this nozzle design is used, and the ambient mass flow rate is analyzed as a function of nozzle pressure, it is found that the flow rate drops uniformly with the decrease in operating pressure. Further, by using this nozzle design, a narrow particle size range can be selected by varying the pressure in the nozzle body, for example, from ambient pressure down to 1 torr.

The overall performance of the nozzle can best be judged by the frequency of particle hits in the mass spectrometer. This involves the size selectivity and transmission efficiency of the nozzle, the probability of hitting a particle once it enters the source region, the volume flow rate into the instrument, and particle number concentration in the aerosol.

The efficiency, $E_h$, is defined as the number of particles analyzed divided by the number of particles entering the source region (assuming that the particle beam is smaller than the laser beam) and is equal to the length of the source region divided by the length that a particle travels between laser shots $$E_h = fL/100v$$

where v (m/s) is the particle velocity, f (Hz) is the firing rate of the laser, and L (cm) is the length of the source region. Particles enter the source region through a sonic nozzle traveling at about 150 to 100 m/s. When the firing rate of the excimer laser is 100 Hz and the length of the source region is 4 cm, the efficiency is about 2%.

The volume flow rate into the nozzle is governed by which particle size is to be selected. When larger particles are sampled, a valve will admit more gas so that the pressure in the nozzle will be higher. When the smaller particles are sampled, the valve admits less gas so the nozzle pressure is lower. The frequency of particle hits is dependent on the transmission rate (cc/min) and the atmospheric concentration of particles at the size selected. The time between particle hits is given by $$t(p) = [\int n(d) T(d;p) dd]^{-1}$$

where n(d) ($cm^{-3}$) is the particle number concentration distribution and T(d;p) ($cm^3$/s) is the nozzle transmission rate into the nozzle as a function of size and at the selected working pressure, p. The number concentration of large particles in the atmosphere is fairly low and under cleaner meteorological conditions or at cleaner locations, it is worthwhile estimating the amount of time that will transpire between particle samples. If we assume that dN/dlogd=1 p/cc and approximate the transmission efficiency as a square wave with geometric standard deviation of 1.3 and height around 10,000 cc/min for 1 micron diameter particles, we obtain samples at a rate of around 1 per second. At 0.1 micron, a particle concentration of 100 p/cc would yield a sampling rate of 1 per second, while at 10 nm a concentration of 1000 p/cc yields a 1 per second sampling rate. Concentrations of particles in urban environments almost always exceed these concentrations by a considerable margin, especially for the smaller particle sizes.

In a highly preferred embodiment of the present invention, the nozzle design used to create the particle beam in the mass spectrometer is any of the types described in U.S. Pat. No. 4,358,302, which issued on Nov. 9, 1982 to Dahneke. The entire disclosure of this patent is hereby expressly incorporated by reference into the present patent application.

In the instrument of the present invention, since each particle is detected by the presence of its spectrum, it is important that particles are analyzed regardless of their composition. Experiments have shown that the 193 nm excimer wavelength is suitable for analyzing all but pure sulfuric acid particles—even a small contamination with ammonia, for example, allows sulfuric acid particles to be analyzed at the 193 nm wavelength. Since particles 10 nm and larger are very unlikely to be pure sulfuric acid the 193 nm wavelength is suitable for particle analysis.

The data system is important to the proper operation of the instrument. Spectra will be acquired at a high rate (e.g., 100 Hz), but for the vast majority of these spectra the laser pulse will not coincide with a particle in the source region so the spectrum will be null. Each firing of the laser generates 32 kb of data (16 kb each for the positive and negative spectra). If all the spectra are saved, any reasonable data storage system will be quickly filled to capacity. Thus, each spectrum must be examined for validity before it is stored.

At the present time, the EISA bus in most PCs is not fast enough to move 32 kb of data in $\frac{1}{100}$ of a second, let alone assess its validity, so hardware must be used to check data validity. The hardware used in a preferred version of the instrument of the present invention was a custom version of Precision Instruments, Inc.'s (Knoxville, Tenn.) 500 MHZ data acquisition board (model 9847). This board performs the data validity check in firmware. The board is triggered for every laser pulse. The first two microseconds are skipped (there is often noise from the laser firing of this portion of the spectrum), and the rest of the spectrum is checked for any points lying above a user-programmable datum. If all points are below the datum, the board is internally reset and the next spectrum overwrites the current one. A logarithmic amplifier is installed between the microchannel plate and the transient digitizer to increase the dynamic range of the system and spread digitation errors more evenly over this range.

If any point is above the datum, subsequent triggers are ignored and a data valid flag is raised. A program on the PC periodically checks this flag. When it is raised, the program copies the spectrum from the A/D boards to disk along with the time the data was recorded and the voltage setting of the DMA (which is also controlled by the PC). Then the program resets the board and operation continues.

EXAMPLES

Figure 10:
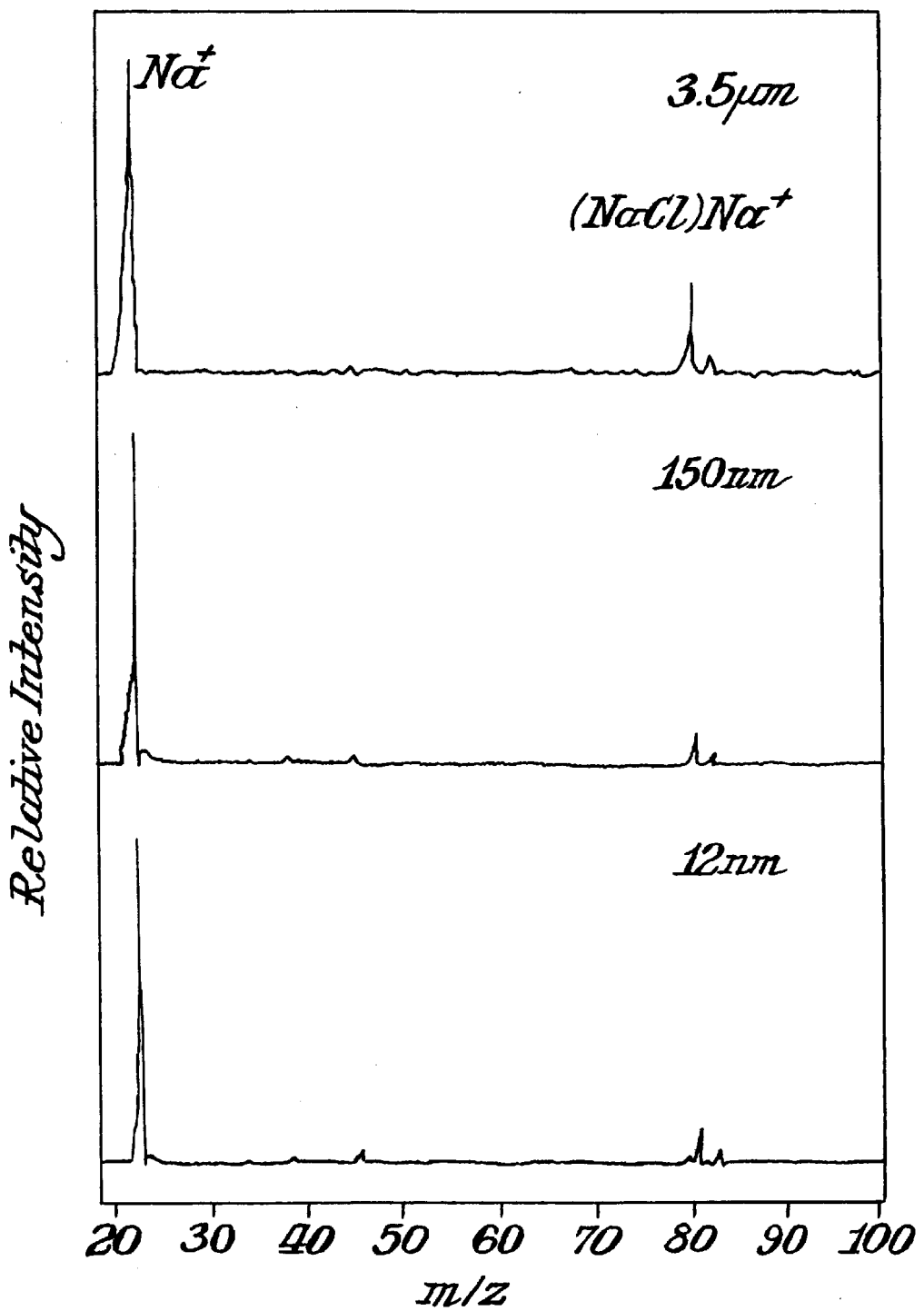
FIG. 10 is the positive ion spectra of NaCl particles having various diameters.

Aerosol particles ranging in size from 12 nm to 3.5 $\mu$m consisting of NaCl, KCl, $NH_4NO_3$ and anthracene were analyzed with the instrument shown in FIG. 6. FIG. 10 shows spectra of 3.5 $\mu$m, 150 nm and 12 nm diameter NaCl particles. The three spectra have the same characteristic peaks, $Na^+$ and $(NaCl)Na^+$, but the relative intensity of $(NaCl)Na^+$ peak decreases as the particle diameter decreases. The 3.5 $\mu$m particles consistently show a large $(NaCl)Na^+$ peak but for 150 nm and smaller particles, the $Na^+$ ion is often the only ion present in the spectrum. This suggests that the cluster ion is produced by ion-molecular reactions in the ablated plume. As the particle size decreases, the plume density also decreases and cluster formation is less probable.

Figure 11:
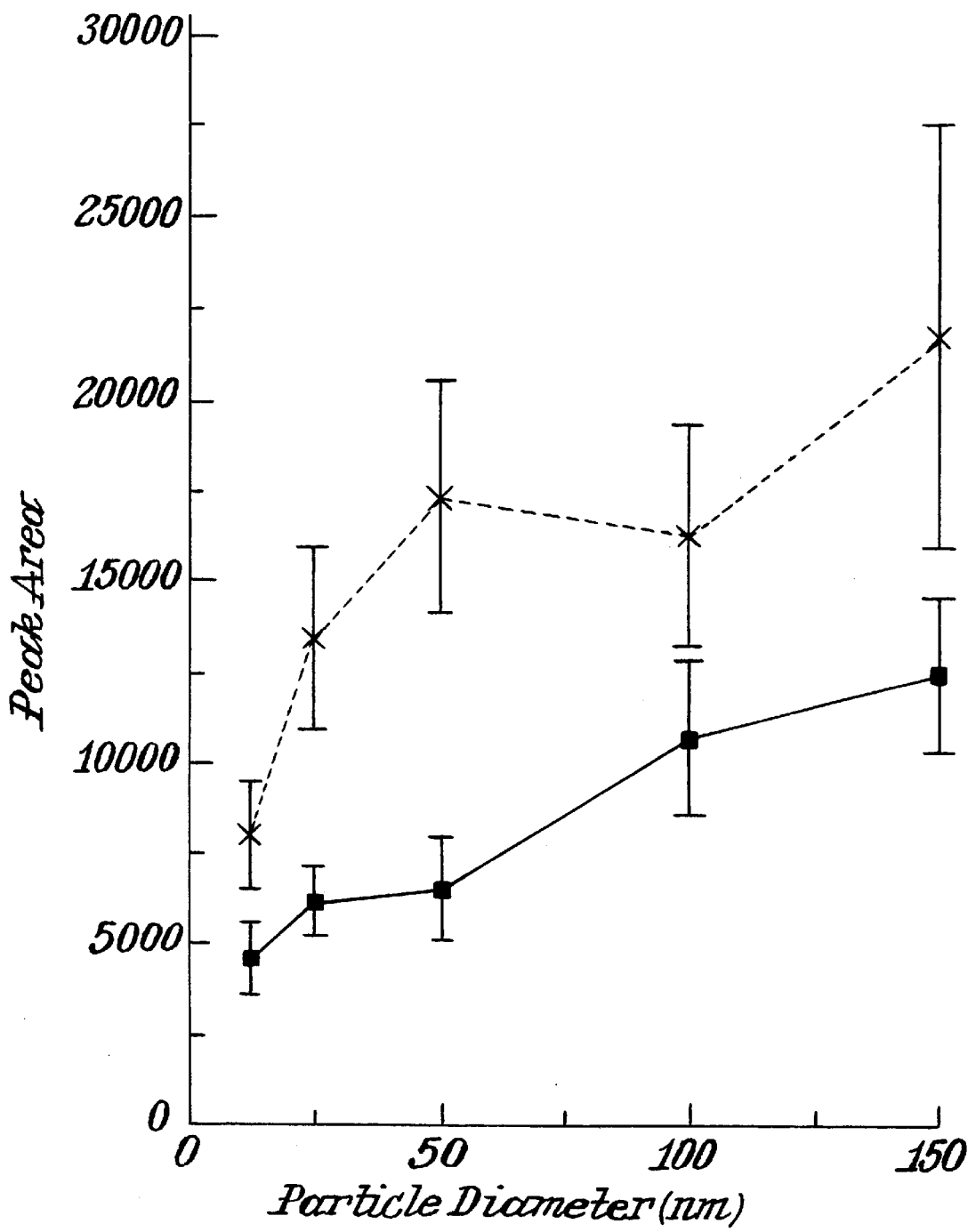
FIG. 11 is a plot of peak area vs. particle diameter for the resultant ions $Na^+$ and $K^+$.

The $Na^+$ and $K^+$ signals from NaCl and KCl particles respectively are plotted versus particle diameter in FIG. 11. For equivalent particle sizes and mass spectrometer settings, the $Na^+$ signal is larger than the $K^+$ signal. The signal for both ions decreases slightly as the particle diameter decreases. One would expect that the intercept of the line would pass through the origin of the graphs, but it does not. The voltages for the detector and the limit test for detection were held constant for all the runs to keep a consistent response from the detector. The discrepancy of the nonzero intercept may arise from the bias of the limit test against low signal intensities. The standard deviation of the peak area is quite large and for the smaller particles, many of the low intensity spectra may register as noise from the limit test and the spectra are not saved.

Figure 12:
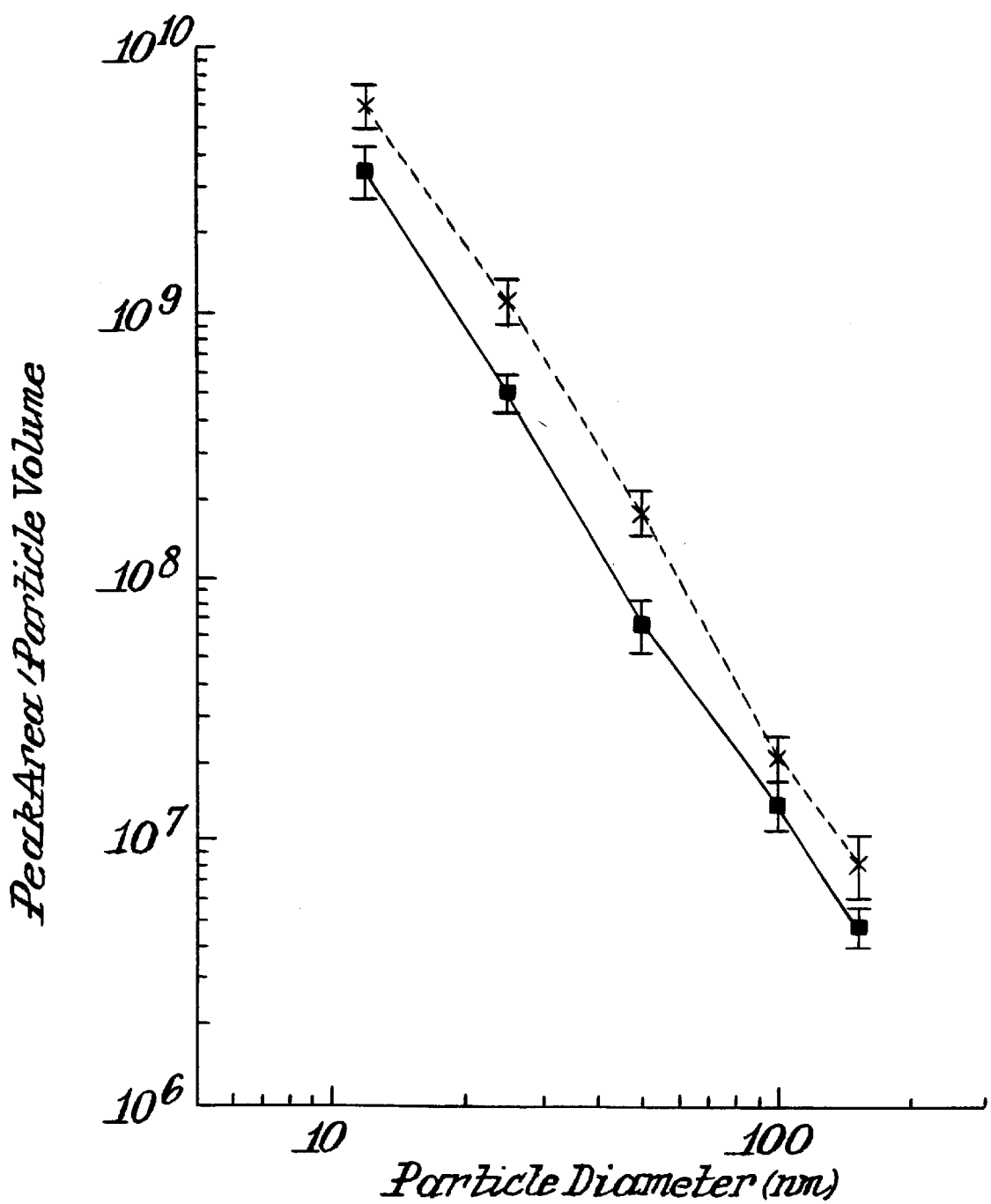
FIG. 12 is a plot of peak area per particle volume vs. particle diameter for the resultant ions $Na^+$ and $K^+$ from NaCl and KCl particles.

A plot of peak area per particle volume vs. particle diameter for the resultant ions $Na^+$ and $K^+$ from NaCl and KCl particles is shown in FIG. 12. The peak areas between 12 nm and 150 nm vary by a factor of 3, while the particle volume varies by a factor of 1000. This shows that larger particles are less efficient at producing ions than smaller particles. This result may be explained by interactions within the plume produced by the laser desorption process. With the larger particles, the ion plume is believed to be more dense. In a dense plume, collisions between positive ions and electrons are enhanced, causing a higher percentage of the ions to become neutralized.

Figure 13:
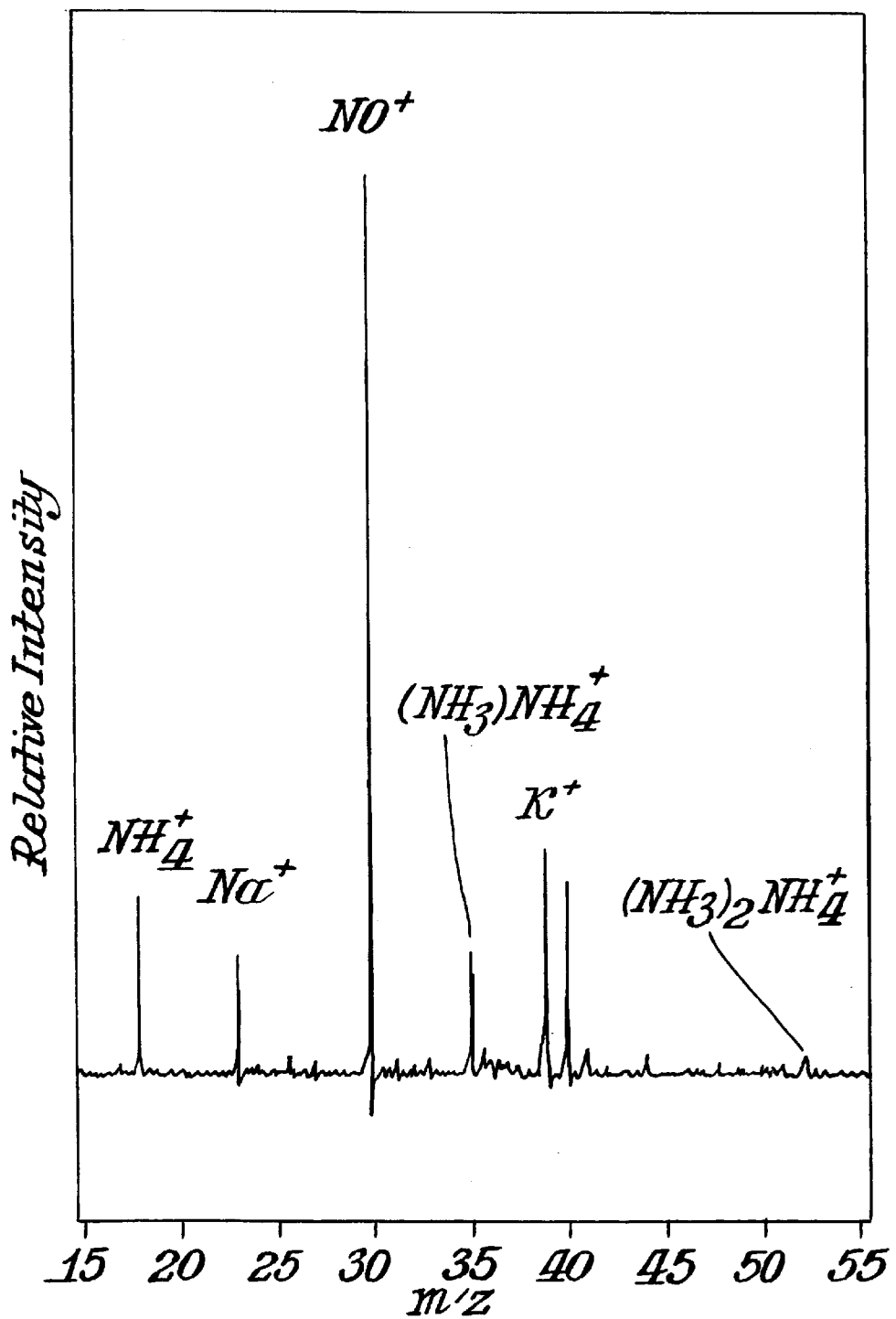
FIG. 13 is the averaged positive ion mass spectrum of twenty 150 nm diameter $NH_4NO_3$ particles.
Figure 14:
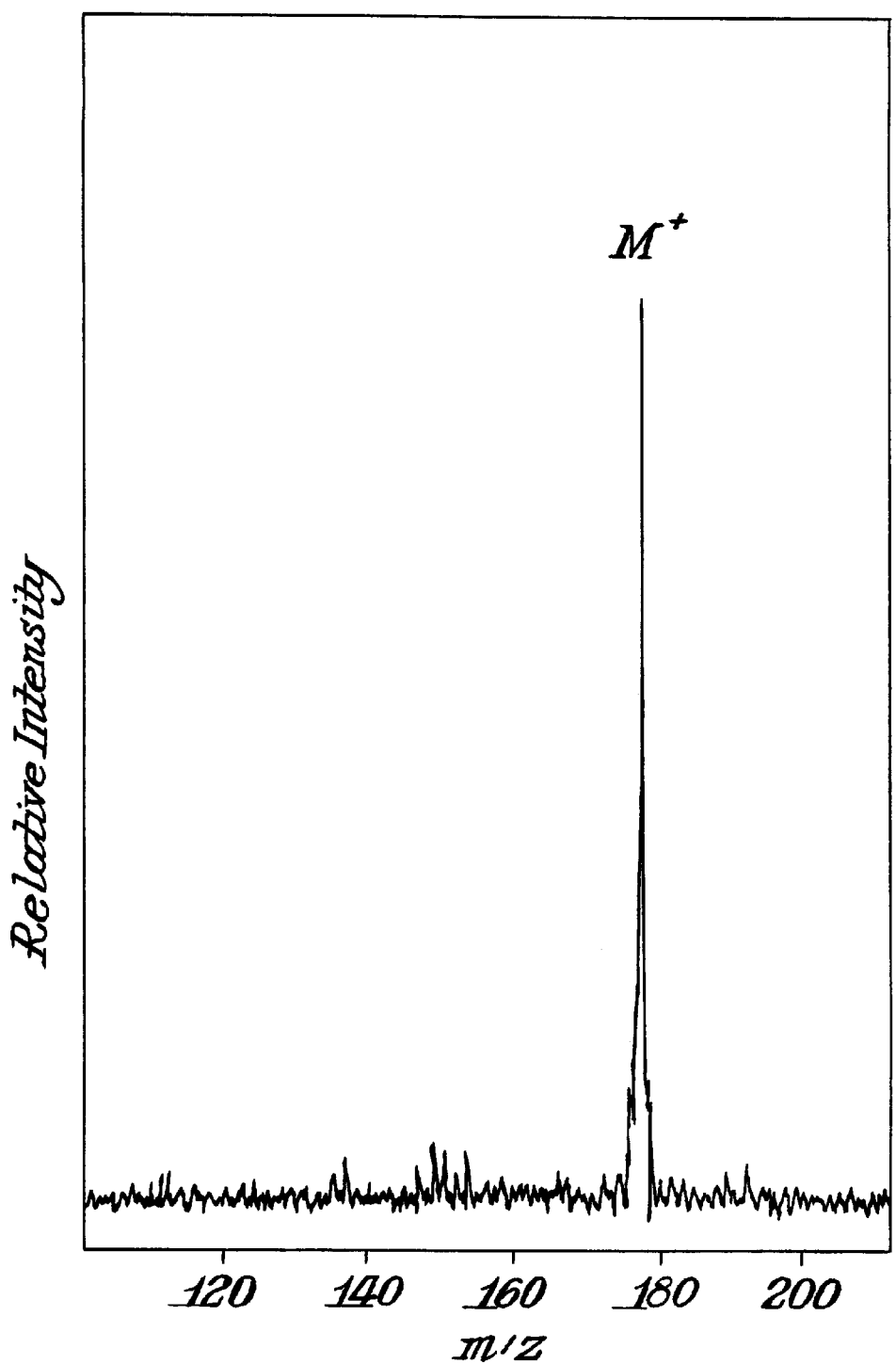
FIG. 14 is the averaged positive ion mass spectrum of twenty 150 nm diameter anthracene particles.

The mass spectra of 150 nm diameter $NH_4NO_3$ and anthracene aerosols are presented in FIGS. 13 and 14. These spectra are the average of 20 individual mass spectra. In FIG. 13, several ions are observed including $NH_4^-$, $NO^-$, $(NH_3)NH_4^+$ and $(NH_3)_2NH_4^+$. These ions are also observed in LAMMA and RSMS spectra of micron size particles. The mass spectrum of anthracene in FIG. 14 was taken with a 10 $\mu$s delay to avoid triggering on contaminant peaks. In the analysis of anthracene, salt contamination leading to the formation of $Na^+$ and $K^+$ plagued the spectra and for most particles only these ions were observed. One benefit of the data system is that the delay for the limit test and/or acquiring spectra can be set past these ions so that particles can be pre-screened for a higher m/z ion. This approach could be used as a filter to analyze only those particles of interest in situations involving heterogeneous aerosols.

The mass resolving power, R, of the instrument of the present invention is usually greater than 150 (R=m/$\Delta$m where m is the mass to charge ratio of an ion peak and $\Delta$m is the full width at the half-max, that is, halfway up the peak).

The spectra taken with the instrument of the present invention can have a shoulder or extra peak on the low m/z side of the main peak, which decreases resolving power.

It is believed that the initial kinetic energy spread of the ions can explain the asymmetry of the peak. This energy originates from the laser ionization process which results in a plume of ions expanding in all directions within the source region. Even a few eV discrepancy in the initial kinetic energy is large enough to cause ions to reach the detector up to several hundred nanoseconds apart. From the shape of the peak, the initial kinetic energy spread of the ions was calculated by the following equation:

$$KE=(0.5)\times(m)\times(\Delta v)^2=9.2\times10^{-20} \text{ J}=2.2 \text{ eV}$$

where KE is the kinetic energy, m is ion mass for $Na^+$ ($3.8\times10^{-26}$ kg) and dv is the difference in the velocity of the ions from the same packet ($4.4\times10^3$ m/s) determined from the ion flight length divided by the width of the peak. When the initial kinetic energy spread is 2.2 eV, the time that it takes ions with initial velocity vectors toward the backing plate to reverse direction and travel towards the detector is small and does not add significant tailing to the peak.

A preferred instrument of the present invention uses an inlet that was designed for high gas throughput. The aerosol is sampled from atmospheric pressure through a 0.5 mm i.d. orifice into a differentially pumped chamber. The total gas flow through the orifice is 1.5 L/min and the pressure in the chamber is maintained at 0.5 torr with a mechanical pump. A 0.5 mm i.d. skimmer is positioned 3.2 mm downstream from the orifice. Since particles have higher momentum than individual gas molecules, the skimmer preferentially transmits particles into a second differentially pumped chamber while the gas molecules are pumped away. The pressure in the second chamber is maintained at 0.01 torr with a second mechanical pump. A second skimmer, 1.0 mm i.d., is positioned 1.27 cm downstream from the first skimmer. Particles passing through the second skimmer travel an additional 24.8 cm to reach the center of the source region of the mass spectrometer. Trle particle beam diverges from the second skimmer to a diameter of ca. 1.3 cm in the center of the source region. The particle beam diameter in the source region was determined from the spatial distribution of particles collected on a glass plate. When an aerosol containing 860 particles/$cm^3$ is sampled into the inlet, the instrument is able to analyze approximately 1 particle every two seconds. Thus, approximately 1 particle is analyzed for every $10^6$ that enter the inlet.

The particle transmission efficiency through the inlet limits the analysis rate for the mass spectrometer. The inlet efficiency ($E_h$) can be calculated by:

$$E_h=(E_a n \text{ V R})^{-1}$$

where $E_a$ is the ablation efficiency, n is the number of particles per unit volume in the aerosol (before the inlet), V is the volume flow rate of aerosol into the inlet (e.g., 30 cm³/s in Example 1), and R is the average number of laser shots required to hit a particle and generate a spectrum. The particle density, n, is dependent on the aerosol source. For the system used in Example 1 with an atomizer coupled to the $^{85}$Kr neutralizer, the particle density ranges between $1.5 \times 10^5$ to 8.4 to $10^6$ particles/cm³ depending upon particle size. For the system described in Example 1, accurate measLurelients of the particle density were obtained in the calibration experiment for the radial DMA.

Figure 15:
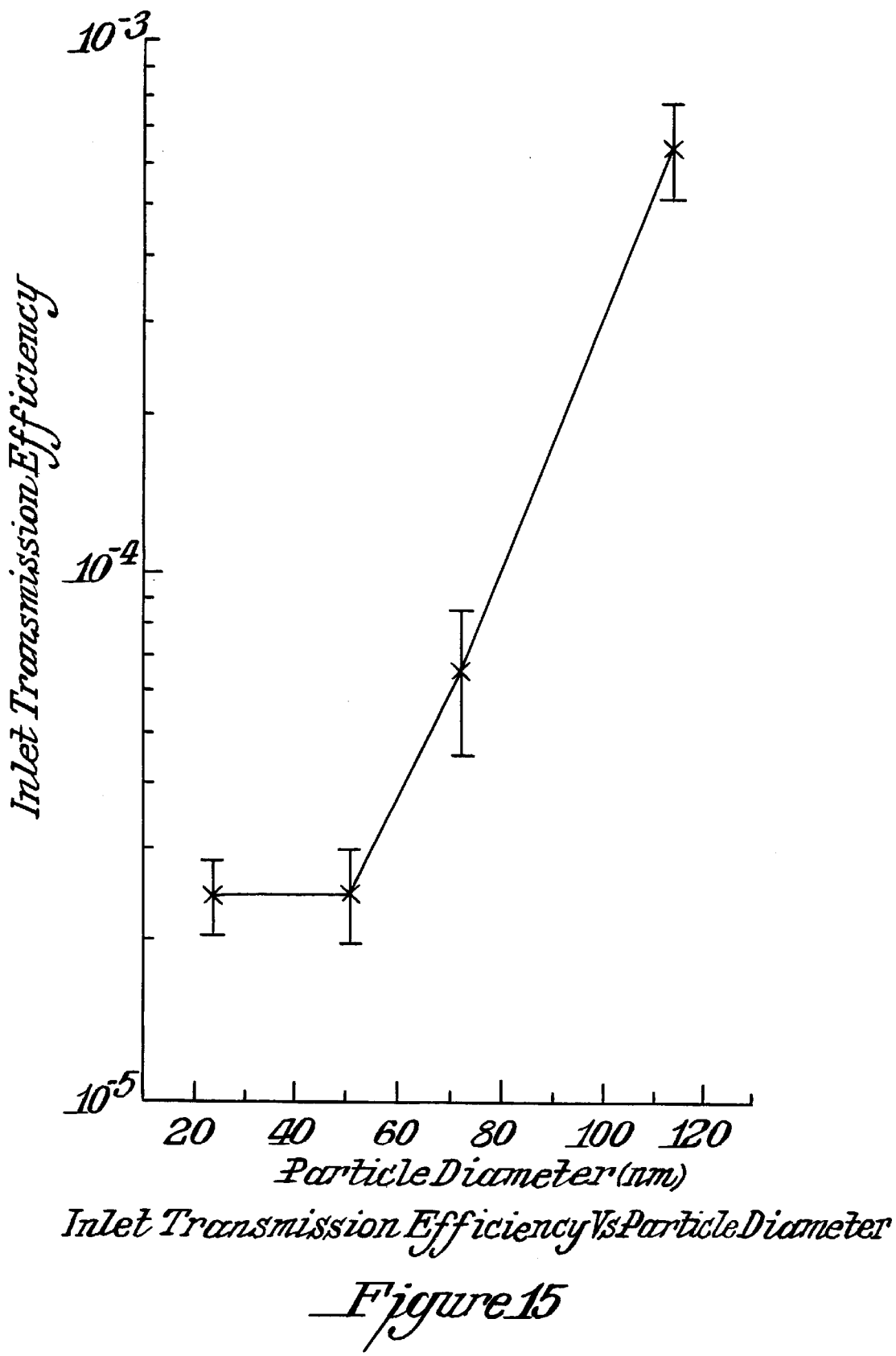
FIG. 15 is a plot of the inlet transmission efficiency vs. particle diameter of the inlet used in Example 1.

FIG. 15 shows the calculated transmission efficiency of the inlet used in Example 1 as a function of particle size for a sheath air flow of 4 L/min. Each data point is the median of forty measurements. The error bars correspond to one standard deviation. FIG. 15 shows that the particle transmission is dependent on particle diameter until the diameter becomes smaller than the mean free path of air. Below this point, the transmission efficiency remains constant.

Figure 16:
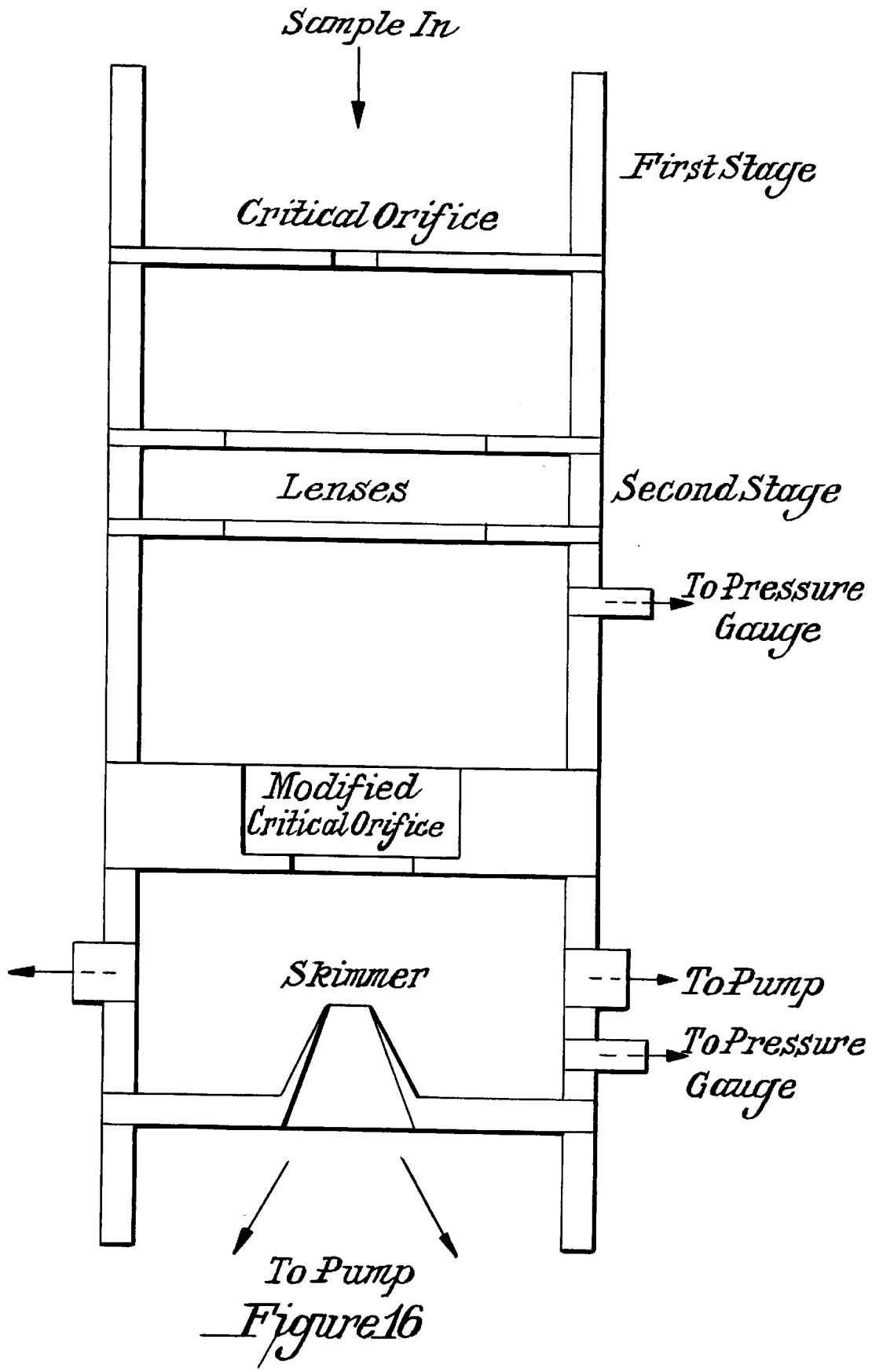
FIG. 16 is a schematic drawing of a preferred inlet for the mass spectrometer of the present invention.

When the inlet transmission efficiency ($E_h$) and ablation efficiency ($E_a$) are both taken into account, the overall efficiency for particle analysis ranges from less than $1 \times 10^{-7}$ for 20–50 nm particles to $2 \times 10^{-6}$ for 120 nm particles. These values are very low and reflect primarily the poor inlet transmission efficiency. This inlet is more appropriate for larger (micron size) particles. A preferred inlet for ultrafine particles includes a series of aerodynamic lenses that force the particles toward the center of the air flow passing through the orifice. A schematic drawing of such a preferred inlet is shown in FIG. 16. It should be noted that there are many possible nozzle designs that would be suitable for the instrument of the present invention. The nozzle design, per se, is not considered to be a crucial element of the present invention. Many nozzle designs that are known in the art would be acceptable for use with the instrument of the present invention. The main requirements for the nozzle are that it should be able to deliver particles of a preselected size to the mass spectrometer in a highly focused beam (i.e., the difference in the diameter of the particle beam from the point the beam exits the nozzle to the center of the source region of the mass spectrometer should be minimized). As discussed earlier, many of the nozzle designs described in U.S. Pat. No. 4,358,302 to Dahneke are acceptable for use in the instrument of the present invention.

Example 1

An instrument for the on-line chemical analysis of aerosol particles was produced as described below.

The instrument comprised a time-of-flight mass spectrometer having the optical layout shown in FIG. 1. A laser beam 1 from an excimer laser 22 (MPB Technologies PSX-100 excimer laser) was free-fired at 30 Hz into a vacuum chamber 5 through a focusing lens 2 mounted in a conflat port 3. Before the laser beam reached the lens 2, it was split by a variable dichromic beam splitter 23 and one part of the split beam was sent to a sensor 24. A mirror 4 was positioned inside the vacuum chamber and was aligned at a 45° angle to reflect the incoming laser beam vertically through the source region 6. A quartz slide 7 was positioned above the mirror to prevent particles from depositing on the mirror surface.

The laser beam was imaged to a small spot (about 600 µm in diameter) in the center of the source region 6 but expanded to a much larger spot (about 2 mm in diameter) at the edges of the source region (shown as 8 and 18 in FIG. 1). The overall length of the source region from 8 to 18 was 4.0 cm.

The particles to be analyzed entered the vacuum chamber 5 through inlet 9 and formed a narrow particle beam having a median beam diameter in the source region of about 0.5 cm. The particle beam was colinear with the portion of the laser beam that passed through the source region 6 but was moving in the opposite direction of the laser beam. When a particle was ablated and ionized by the laser beam in the source region 6, the ions that were formed were accelerated by a system (described below) down the flight tube 11 towards the detector system 12. The flight tube was 1.1 meters long, had a nominal outside diameter of 4 inches and was made of stainless steel. The ion acceleration system consisted of a repeller plate 10, an acceleration plate 13 and a grounding plate 14 with a ½ inch spacing between the plates. The potentials across the plates are given in Table 2 for both positive and negative ion modes.

TABLE 2

Voltages for Mass Spectrometer Operation

| Electrode | Voltages in positive ion mode | Voltages in negative ion mode |
| --- | --- | --- |
| Repeller plate | +5000V | −5000V |
| Acceleration plate | +2700V | −2700V |
| Drift tube | 0V | 0V |

The repeller plate 10, acceleration plate 13 and grounding plate 14 were made of 4.4 cm by 7.5 cm stainless steel plates. The acceleration plate 13 and grounding plate 14 both had a ½ cm by 5 cm centered rectangular (cut-out) hole that was covered by a 90% transmittance wire mesh 16. The wire mesh was spot welded to the plate over the hole. The wire mesh was used to reduce the electric field distortions.

The detector system 12 consisted of a first microchannel plate 17, a second microchannel plate 19 and an anode 20. The first and second microchannel plates 17 and 19 were obtained from (R. M. Jordan and Co., Grass Valley, Calif., Part No. C-701). The first microchannel plate 17 had the highest voltage applied across the plate, the second microchannel plate 19 had the second highest voltage applied across the plate and the anode 20 had the lowest voltage. The potentials across the plates are given in Table 3 for both positive and negative ion modes.

TABLE 3

| Electrode | Voltages in positive ion mode | Voltages in negative ion mode |
| --- | --- | --- |
| First microchannel plate | −2200V | −2200V |
| Second microchannel plate | −1200V | −1200V |
| Anode | 0V | 0V |

In FIG. 1, the break 21 is used to indicate that a section of flight tube 11 is missing from the figure.

A schematic of the overall system used to analyze the particles discussed below is shown in FIG. 6. The position of the laser in FIG. 6 has been reversed with respect to the flight tube for convenience purposes and to show that the position of the laser is not important as long as the laser beam ultimately passes through the source region in a colinear manner with the particle beam.

In FIG. 6, it can be seen that a radial differential mobility analyzer (DMA) has been used in a position so that the DMA feeds particles to the inlet of the mass spectrometer. A detailed cross-sectional view of the radial differential mobility analyzer used in this example is shown in FIG. 3.

A detailed schematic of the poly-disperse aerosol generator shown in FIG. 6 is provided in FIG. 2.

The system shown in FIG. 6 was used to analyze an aerosol containing NaCl particles having an average particle size of 12 nm. As shown in FIG. 2, the particles were produced with an atomizer by forcing compressed dry air at 35 psi into a solution of NaCl particles in water contained in a flask and then drawing off the mist formed above the solution. This mist, which was flowing at 3.5 L/min, was then mixed with an additional 7.0 L/min of dry air to dry the primary droplets produced from the atomizer. The combined flow of mist and dry air (10.5 L/min) was then provided to a $^{85}$ Kr neutralizer (TSI, Inc. St. Paul, Minn., Part No. 3012). The output from the $^{85}$ Kr neutralizer was split into two flows by a flow tee. A flow of the NaCl aerosol at 1 L/min was provided to the aerosol flow inlet of the DMA while a flow of NaCl aerosol at 9.5 L/min was sent to a vent through a regulating valve and a flowmeter. A flow of 2 L/min of dry air was provided to the sheath entrance on the DMA at the same time that the flow of NaCl aerosol at 1 L/min was provided to the aerosol flow inlet of the DMA. The electrode in the radial DMA had an applied voltage of 50 volts during use. The DMA provided a 1 /min aerosol flow to the inlet of the mass spectrometer. The aerosol flow contained a narrow particle size range wherein virtually all of the particles had a size of about 12 nm. When the aerosol flow from the DMA passed into the inlet of the mass spectrometer, the air that was transporting the particles was drawn off as the particles passed through the nozzle and were forced into a narrow particle beam. This particle beam entered the mass spectrometer and passed through the source region, where some of the particles were ablated and ionized by the laser beam. The ions from the ablated particles traveled down the flight tube and were detected by the detector system which then sent a signal through an amplifier to a Tektronix 520A oscilloscope which was sampling 15 Kb record lengths at 30 Hz. The spectra obtained by the oscilloscope were digitized by the oscilloscope and checked to see if any peak registered above a minimum threshold. When the oscilloscope registers a peak above the threshold value, the oscilloscope transfers the spectrum to a computer for storage. Although the system shown in FIG. 6 uses the computer to control the power settings of the disk electrode in the DMA, and the repeller plate, accelerator plate and the detector in the mass spectrometer, these power settings could be set by other means known in the art.

The oscilloscope also controls the firing rate of the excimer laser.

In the system used in the present example, a data acquisition program written in Visual Age C++ coordinates the size of the aerosol entering the mass spectrometer with the mass spectra by saving the DMA voltage setting into the mass spectrum's filename. All power supplies used for the mass spectrometer and the differential mobility analyzer are controlled with the analog output from a digital to analog converter (DAC) controlled by the computer program. The DAC and the oscilloscope communicate with the computer through an IEEE488.2 interface. FIG. 6 shows a schematic diagram of the mass spectrometer showing the peripheral data lines. The IEEE parallel port interface is chosen to link the computer with the DAC and the oscilloscope because of its relatively high bandwidth and flexibility.

Figure 17:
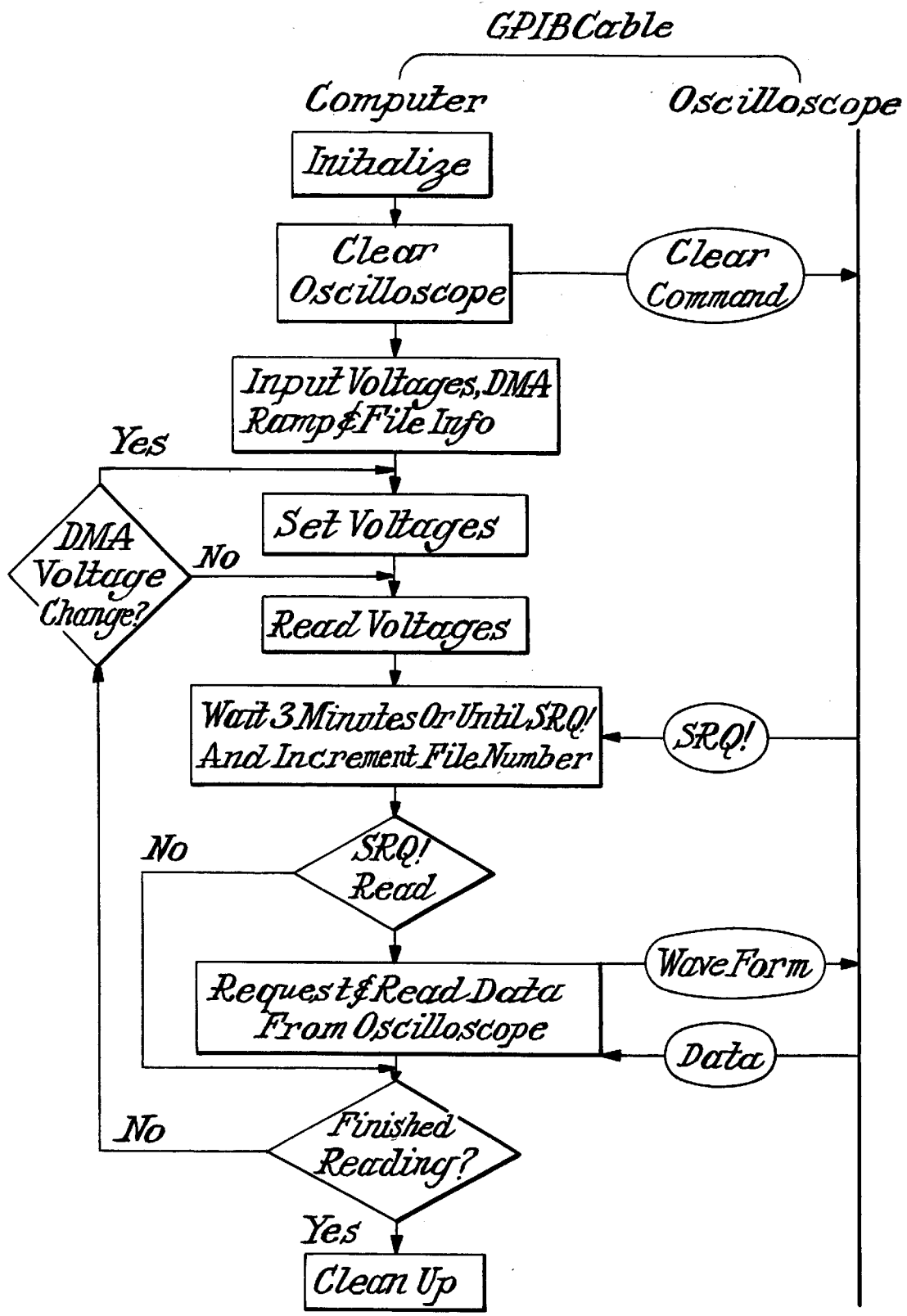
FIG. 17 is a flow chart for the data acquisition software program used in Example 1.

The flow chart for the program is shown in FIG. 17. The program starts by initializing the IEEE488.2 interface with the DAC and the oscilloscope. Next, a window appears in which the voltages for the DMA, Backing Plate, Detector and the XY Deflection Plate voltages can be input. To test the communication between the computer program and the DAC, the Test LED button is used to toggle an LED on the front panel of the DAC to insure proper communication. The Set Voltages button takes the text value from a box on the window called an IEntry field for the DMA, Backing Plate, XY Deflector and the Detector and sets the corresponding power supplies to those values. These voltages are often set at this stage of the program to insure the oscilloscope is scanning properly. The Reset button zeros all of the power supplies.

The DMA can run in a static (fixed) or a dynamic (scanning) mode when spectra are being acquired. The program has been written so that any DMA voltages between 0V to 10,000V in any order can be entered for arbitrary lengths of time.

To check against systematic errors, the operator can enter a set of DMA voltages to scan and repeat this or any other sequence up to 24 times, and the program identifies the run parameters in the file name. The filename format consists of directory information, filename prefix, DMA voltage setting, a character starting with A, file number and ".wft" extension. If the same DMA voltage is used twice, then on the second iteration the character A will be changed to B and the character increments for each time the same DMA voltage is called. The filename would typically look as follows: D:\SPECTRA\NACL5000C2491.WFT. Where D:\SPECTRA\NACL\ and NACL is the directory information and filename entered in the File Info. menu. The number 5000 is the DMA voltage setting, C indicates that this is the third time the DMA has been set to 5000 in this run and 2491 is the number of spectra taken during this DMA setting.

After the output voltages of the power supplies have been checked, the program waits for up to three minutes for a service request (SRQ) for the oscilloscope. If within this time period a spectrum read by the oscilloscope is greater than the minimum intensity of the template, the oscilloscope will send out a service request signal. The SRQ prompts the data collection program to download the spectrum to the computer. At this point the program sends a string of commands instructing the oscilloscope to send the spectrum in ASCII-Y format through the IEEE parallel port. The computer program then reads the data from the IEEE port and transfers it to a hard disk in the computer for storage. If during the three minute time period a spectrum has not been detected by the oscilloscope, the program skips the request data step and continues to increment the file name by one. At this point the program checks to see if any other spectra need to be saved at the current DMA setting or any other DMA settings. If so, the program goes back to make sure the power supplies are at the correct voltage and continue the cycle of waiting for spectra from the oscilloscope. After all of the spectra have been saved, the program exits the run menu and returns to the main window.

The same procedure described above was performed with 150 nm and 3.5 $\mu$m NaCl particles. The positive ion spectra that were obtained for all of these particles is shown in FIG. 10.

The functions of the software used to calibrate the instrument and collect the data generated by the instrument described in detail above. From the above description, an artisan of ordinary skill would be able to write the software necessary to run any instrument that uses the novel features of the present invention. The specific software used does not constitute part of the best mode of the present invention.

While the invention has been particularly shown and described with reference to preferred embodiments thereof, it will be understood by those skilled in the art that various changes in form and details may be made without departing from the spirit and scope of the invention as defined in the appended claims.

What is claimed is:

1. An apparatus for detecting, sizing or otherwise analyzing particles comprising:
   (a) a beam of particles, wherein said particles have diameters in the range of from about 10 µm to 10 nm,
   (b) a detector;
   (c) a radiation source which transmits a beam of radiation into a source region so that said beam of radiation and said beam of particles are collinear in said source region and said beam of radiation contacts said beam of particles in said source region, wherein said beam of radiation has an intensity which is sufficient to heat at least one particle from said beam of particles to a temperature which is sufficient to vaporize and ionize said at least one particle in the source region, further wherein ions from a particle that has been vaporized and ionized by the radiation beam in said source region are accelerated towards said detector so that at least a portion of said ions will contact said detector.

2. The apparatus of claim 1, wherein said beam of particles is formed by a particle inlet.

3. The apparatus of claim 1, wherein said radiation source is a laser.

4. The apparatus of claim 1, wherein said beam of radiation is a laser beam.

5. The apparatus of claim 1, wherein the beam of radiation and the beam of particles are collinear and moving in opposite directions in the source region.

6. The apparatus of claim 5, wherein at least a portion of the particles in the beam of particles collide in a head-on manner with the beam of radiation in the source region.

7. A process for detecting, sizing or otherwise analyzing particles comprising the following steps:
   a) supplying particles to an apparatus that comprises a source region and a detectors wherein said particles have diameters in the range of from about 10 µm to 10 nm;
   b) forming a beam of particles from at least a portion of said particles and directing said beam of particles so that said beam of particles passes through said source region;
   c) transmitting a beam of radiation into the source region so that the beam of radiation is collinear with said beam of particles in said source region;
   d) contacting at least one particle from said beam of particles with said beam of radiation in said source region so as to vaporize and ionize said at least one particle in the source region;
   e) accelerating ions from a particle that has been vaporized and ionized by the radiation beam in said source region towards said detector so that at least a portion of said ions will contact said detector; and
   f) detecting the ions that contact said detector with said detector.

8. An apparatus for analyzing particles comprising:
   a) a mass spectrometer having a particle inlet, a source region and a detector; and
   b) a radiation source which transmits a beam of radiation into the source region of said mass spectrometer;
   wherein a beam of particles having diameters in the range of from about 10 µm to 10 nm passes through said particle inlet into said source region of said mass spectrometer so that said beam of particles is collinear with said beam of radiation in said source region and contacts said beam of radiation in said source region, said beam of radiation having an intensity which is sufficient to heat at least one particle from said beam of particles to a temperature which is sufficient to vaporize and ionize said at least one particle in the source region of said mass spectrometer, further wherein ions from a particle that has been vaporized and ionized by the radiation beam in said source region are accelerated towards said detector so that at least a portion of said ions will contact said detector.

9. The apparatus of claim 8, wherein said radiation source is a laser.

10. The apparatus of claim 8, wherein said beam of radiation is a laser beam.

11. The apparatus of claim 10, wherein the laser beam enters the mass spectrometer in a first direction and contacts a device which changes the first direction of the laser beam to a second direction.

12. The apparatus of claim 11, wherein the device is at least one mirror.

13. The apparatus of claim 8, wherein the beam of radiation and the beam of particles are collinear and moving in opposite directions in the source region.

14. The apparatus of claim 13, wherein at least a portion of the particles in the beam of particles collide in a head-on manner with the beam of radiation in the source region.

15. A process for analyzing particles comprising the following steps:
   a) supplying a gas containing particles to a mass spectrometer having a particle inlet, a source region and a detector, wherein said particles have diameters in the range of from about 10 µm to 10 nm;
   b) passing the gas through the inlet wherein at least a portion of the particles in the gas are separated from the gas and formed into a beam of particles that passes through the source region;
   c) transmitting a beam of radiation into the source region so that the beam of radiation is collinear with said beam of particles in said source region;
   d) vaporizing and ionizing at least one particle from said beam of particles with said beam of radiation in said source region to produce ions;
   e) accelerating said ions towards a detector so that at least a portion of said ions will contact said detector.

* * * * *